(12) United States Patent
Chang

(10) Patent No.: US 7,683,332 B2
(45) Date of Patent: Mar. 23, 2010

(54) INTEGRATED SINGLE PHOTON EMISSION COMPUTED TOMOGRAPHY (SPECT)/TRANSMISSION COMPUTED TOMOGRAPHY (TCT) SYSTEM FOR CARDIAC IMAGING

(75) Inventor: Wei Chang, Lisle, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 12/001,000

(22) Filed: Dec. 7, 2007

(65) Prior Publication Data

US 2008/0137806 A1 Jun. 12, 2008

Related U.S. Application Data

(60) Provisional application No. 60/869,274, filed on Dec. 8, 2006.

(51) Int. Cl.
*G01T 1/166* (2006.01)
(52) U.S. Cl. .................................................. 250/363.04
(58) Field of Classification Search . 250/363.01–363.1, 250/370.01–370.15; 378/98.8
See application file for complete search history.

(56) References Cited

U.S. PATENT DOCUMENTS

| | | | | |
|---|---|---|---|---|
| 5,523,571 | A * | 6/1996 | Velazquez et al. | 250/363.05 |
| 6,949,748 | B2 * | 9/2005 | Ziock et al. | 250/370.01 |
| 2003/0031296 | A1 * | 2/2003 | Hoheisel | 378/98.8 |
| 2004/0251419 | A1 * | 12/2004 | Nelson et al. | 250/370.09 |
| 2005/0056788 | A1 * | 3/2005 | Juni | 250/363.04 |
| 2006/0109952 | A1 * | 5/2006 | Chen | 378/4 |
| 2006/0173302 | A1 * | 8/2006 | Conwell | 600/436 |

OTHER PUBLICATIONS

Hoppin et al., "Evaluating estimation techniques in medical imaging without a gold standard: Experimental Validation," 2003, The Proceedings of SPIE, vol. 5034, pp. 230-237.*
Haawman et al., "Line array transmission sources for SPECT attenuation correction—Design and reconstruction", 2005, Proceedings of SPIE, vol. 5745, pp. 79-89.*

* cited by examiner

*Primary Examiner*—David P Porta
*Assistant Examiner*—Kiho Kim
(74) *Attorney, Agent, or Firm*—Iandiorio Teska & Coleman

(57) ABSTRACT

This invention features an integrated single photon emission computed tomography (SPECT)/transmission computed tomography (TCT) system for cardiac imaging including an open arc-shaped frame. A collimator system is shaped to approximately match the thoracic contour of patients having different sizes and weights and shaped to surround and position the collimator closely proximate a heart of a patient of said patients encompassed by at least one predetermined image volume for optimizing collimation of radiation photons emitted from the heart. An arc-shaped detector system is coupled to the collimator subsystem having a shape closely matching the shape of the collimator subsystem for detecting collimated radiation photons from the collimator subsystem and generating output electrical signals. A patient positioning subsystem positions a patient to a predetermined central longitudinal axis of the three-dimensional imaging volume and for intermittently and incrementally rotating the patient about the predetermined central longitudinal axis for generating a plurality of TCT images.

39 Claims, 20 Drawing Sheets

INTEGRATED SINGLE PHOTON EMISSION COMPUTED TOMOGRAPHY (SPECT)/TRANSMISSION COMPUTED TOMOGRAPHY (TCT) SYSTEM FOR CARDIAC IMAGING

RELATED APPLICATIONS

This application claims the benefit of U.S. Provisional Application No. 60/869,274, filed Dec. 8, 2006, which is incorporated by reference herein.

FIELD OF THE INVENTION

This subject invention relates to an improved single photon emission computed tomography (SPECT) with an integrated transmission computed tomography (TCT) subsystem for cardiac imaging.

BACKGROUND OF THE INVENTION

SPECT systems are often used to show the distribution of a radioactive substance inside a patient's body. A source of penetrating radiation is administered to the patient, which typically consists of a pharmaceutical tagged with a radionuclide which emits radiation photons (radiopharmaceutical). The radiopharmaceutical is designed to be absorbed in a target organ, such as the heart muscle, or other organs or body part of interest. The emitted radiation photons are collimated with a collimator subsystem and detected by a detector subsystem which generates output electrical signals which are digitized and processed by a computer system to generate images of the regional distribution of the radioactive sources in and around the target organ.

TCT systems are typically used for obtaining images, or more precisely, the distribution (maps) of attenuation coefficient, in the human body. It has been generally accepted in the field of nuclear imaging that quantitative SPECT imaging requires proper attenuation correction, which in turn requires appropriate attenuation maps to facilitate its correction. The general way to derive these attenuation maps requires the use of TCT, which yields CT images that are converted to appropriate attenuation maps. As a result of this requirement, many modern SPECT systems come with a TCT system to allow TCT imaging to be performed either simultaneously with or sequential to the SPECT imaging. Such systems are referred to here as integrated SPECT/TCT systems, in contrast to recently introduced Hybrid SPECT/CT systems that combine a conventional SPECT with an independent x-ray-CT in the same granty.

One prior SPECT system of a typical SPECT/TCT system proposed by the inventor hereof utilizes a large circular shape design for the frame, or the gantry, collimator subsystem, and the detector subsystem which attempted to accommodate a large patient cross-section while placing the patient's heart at the geometric center for imaging from multiple directions simultaneously. However, because of the off-center location of heart, the circular geometry had to be fairly large to enclose a large patient's thorax. As a result, the long-distance collimation offsets the potential gain in geometric efficiency and renders the circular design less than optimum. Furthermore, the design devoted considerable collimator and detector area to the patient's right-posterior side, where the heart is too distant from the collimator for effective collimation. The typical problem of low photon sensitivity in SPECT is further compounded in cardiac imaging where the desirable radiation photons are scarce: only about 2-4% of the injected dose is in the myocardium of the heart. This previous circular design approach results in a limited return of the heavily attenuated and scattered photons and sub-optimal image quality.

The TCT system of a typical conventional SPECT/TCT system utilizes either a scanning line source of radiation, e.g., $Gd^{155}$, or multiple lines sources stationary with respect to the gamma camera detector to create parallel photon-beams toward a patient to derive a transmission projection, simultaneously with a corresponding emission projection acquisition. These transmission projections, accumulated over a large number of directions, as the gamma camera rotates to meet the sampling requirements, are reconstructed to yield the attenuation maps. The drawback of this approach is that the photon statistics is quite poor because the finite flux of the relative narrow parallel-beam of radiation has to be spread over a large detector area.

Another type of TCT system of a SPECT/TCT system uses a stationary line source to provide a three-dimensional symmetrical or asymmetrical fan beam of photons, or a point source to provide a cone-beam, of radiation photons, towards a patient. A gamma camera located behind the patient includes a matched fan-beam or come-beam collimator for collimating the transmitted photons. The detector system detects the photons and outputs electrical signals and computer system generates TCT images based on the detected photons, after the camera and the source rotate around the patient in a sequential acquisition to the SPECT imaging. However, the problem with these SPECT/TCT systems is the required special collimation that either cannot be fully utilized in emission imaging of the heart, or the systems require a cumbersome and time-consuming collimator exchange procedure, which disturbs the imaging position of the patient and makes the subsequent matching of SPECT and TCT slices for attenuation correction difficult.

The collimator subsystems of typical conventional SPECT/TCT systems are designed with only one predefined set of collimation parameters for both SPECT and TCT imaging. However, such a design compromises either SPECT or TCT imaging. For different SPECT imaging requirements, or for patients having different sizes, a different set of collimation parameters is often needed. Therefore a different collimator with different collimation parameters is needed. Changing collimator, not only is awkward, cumbersome, time-consuming, and unrealistic in clinical environment, it is also difficult to reproduce patient imaging position after the collimator has been changed. The reproducibility of patient imaging position is critical when implementing attenuation correction and guiding image fusion.

The result is conventional SPECT/TCT systems are not flexible in accommodating different SPECT collimation requirements to suit various clinical situations and patients having different sizes and do not provide adequate TCT images needed for attention maps for high quality SPECT imaging. Such a limitation compromises either SPECT or TCT imaging, which in turn limits the attainable quality of attenuation-corrected SPECT imaging.

Another conventional SPECT/TCT system combines an independent x-ray CT, ranging from primitive low-end versions to expensive high-end multi-slice Spiral CTs, to the SPECT system, and are often referred to as Hybrid SPECT/CT systems. The concern of using this approach for cardiac SPECT/TCT is the cost, because an additional dedicated x-ray detector system is required, even for the primitive low-end CTs. As for the use of an expensive high-end multi-slice Spiral CT for attenuation of cardiac SPECT, it is still controversial and is not cost efficient. This latter approach is really intended for other clinical diagnostic applications, such as calcium scoring in cardiac vessels and/or detailed anatomic correlation for other imaging tasks in other regions of the body, rather than for attenuation correction of cardiac SPECT. In fact, due to the mismatch of the acquisition speeds of SPECT and high-end CT, e.g., 10 to 20 minutes for SPECT, verses about 1 to 2 seconds for TCT, the attenuation maps derived by high-end CT have to be further processed to include breathing motion before application. This processing is not trivial and is a potential source of artifacts and suboptimal correction.

Additionally, conventional SPECT systems of prior SPECT/TCT systems typically incrementally rotate the large, heavy collimator and the detector subsystem about the patient to obtain a plurality of projection images (projections). Each time the collimator and the detector subsystem are rotated step-by-step, the collimator and detector follow the patient's body contour by successively adjusting their radial and lateral positions. Such a technique is cumbersome, not easily reproducible, prone to both mechanical and electrical errors, slow, inefficient, utilizes expensive hardware to rotate large heavy collimator and detector subsystems, and requires extensive safety measures to protect the patient. As a result, conventional SPECT images have large variations in image quality and reproducibility, which make comparison of images from different facilities or from different times at the same facility difficult.

BRIEF SUMMARY OF THE INVENTION

It is therefore an object of this invention to provide an improved integrated SPECT/TCT system for cardiac imaging.

It is a further object of this invention to provide such an integrated SPECT/TCT system for cardiac imaging in which the shape of the collimator and detector subsystems optimize detection of radiation photons emitted from the heart.

It is a further object of this invention to provide such an integrated SPECT/TCT system for cardiac imaging which provides a plurality of predetermined imaging volumes of various sizes and locations for optimizing acquisition and image quality.

It is a further object of this invention to provide such an integrated SPECT/TCT system for cardiac imaging which provides high quality SPECT and TCT images for patients having different sizes and shapes in a typical patient population.

It is a further object of this invention to provide such an integrated SPECT/TCT system for cardiac imaging which positions a heart to a desired location based on a previous scout image to optimize SPECT imaging.

It is a further object of this invention to provide such an integrated SPECT/TCT system for cardiac imaging which provides a plurality of collimation parameters.

It is a further object of this invention to provide such an integrated SPECT/TCT system for cardiac imaging which eliminates the problems associated with moving a collimator and a detector subsystem about a patient.

It is a further object of this invention to provide such an integrated SPECT/TCT system for cardiac imaging which is easier to use.

It is a further object of this invention to provide such a integrated SPECT/TCT system for cardiac imaging which provides images that are reproducible at different facilities.

It is a further object of this invention to provide such a integrated SPECT/TCT system for cardiac imaging which provides images that are reproducible at different times at the same facility.

It is a further object of this invention to provide such an integrated SPECT/TCT system for cardiac imaging that is less expensive.

It is a further object of this invention to provide such an integrated SPECT/TCT system for cardiac imaging which improves imaging spatial resolution for a given sensitivity.

It is a further object of this invention to provide such an integrated SPECT/TCT system for cardiac imaging for cardiac imaging which improves sensitivity for a given imaging spatial resolution.

It is a further object of this invention to provide such an integrated SPECT/TCT system for cardiac imaging which can utilize a small point source of radiation to provide a flux of radiation photons.

It is a further object of this invention to provide such an integrated SPECT/TCT system for cardiac imaging which can utilize an X-ray tube to provide a flux of radiation photons.

It is a further object of this invention to provide such an integrated SPECT/TCT system for cardiac imaging in which the source of radiation photons can be turned off and on and the radiation flux can be modulated as needed, such as to patient size.

It is a further object of this invention to provide such an integrated SPECT/TCT system for cardiac imaging which reduces environmental hazards.

It is a further object of this invention to provide such an integrated SPECT/TCT system for cardiac imaging which is safer.

It is a further object of this invention to provide such an integrated SPECT/TCT system for cardiac imaging in which the source of radiation photons is easier to replace.

It is a further object of this invention to provide such an integrated SPECT/TCT system for cardiac imaging in which the source of radiation photons is easier to handle.

It is a further object of this invention to provide such an integrated SPECT/TCT system for cardiac imaging which is easy to implement.

It is a further object of this invention to provide such an integrated SPECT/TCT system for cardiac imaging which can position the patient about a center of a three-dimensional imaging volume to improve TCT images.

It is a further object of this invention to provide such an integrated SPECT/TCT system for cardiac imaging which can provide TCT images for large patients.

The subject invention, however, in other embodiments, need not achieve all these objectives and the claims hereof should not be limited to structures or methods capable of achieving these objectives.

This invention features an integrated single photon emission computed tomography (SPECT)/transmission computed tomography (TCT) system for cardiac imaging including an open arc-shaped frame. A collimator system is shaped to approximately match the thoracic contour of patients having different sizes and weights and shaped to surround and position the collimator closely proximate a heart of a patient of said patients encompassed by at least one predetermined image volume for optimizing collimation of radiation photons emitted from the heart. An arc-shaped detector system is coupled to the collimator subsystem having a shape closely matching the shape of the collimator subsystem for detecting collimated radiation photons from the collimator subsystem and generating output electrical signals. A patient positioning subsystem positions a patient to a predetermined central longitudinal axis of the three-dimensional imaging volume and for intermittently and incrementally rotating the patient about the predetermined central longitudinal axis for generating a plurality of TCT images.

In one embodiment, the shape of the collimator subsystem and the detector subsystems may optimize collimation and detection of the radiation photons for a majority of the patients of a patient population. The predetermined imaging volume may include a three-dimensional cylindrical imaging volume. The arc-shaped frame, the collimator system, and the detector subsystem may be subtended at an angle in the range of about 180° to 220° with respect to the center of the predetermined imaging volume. The collimator subsystem may include a slit-plate comprising a predetermined number of spaced longitudinal slits each having a predetermined width for transversely collimating the radiation photons. The predetermined width of each of the plurality of spaced longitudinal slits may be configured to adjust spatial resolution of transverse collimation. The system may include a plurality of slit-guides attached proximate each side of each of the plurality of longitudinal slits. The angle of the slit-guides and the location of the spaced longitudinal slits may be configured to provide a plurality of non-overlapping projections which define the size and location of the at least one predetermined imaging volume. The size and location of the at least one predetermined image volume and the plurality of non-overlapping projections may provide high geometric efficiency in the detection of radiation photons emitted from the heart. The at least one predetermined image volume may be configured for patients having different thoracic contours and/or different sized hearts and/or different locations of the heart relative to a predefined central axis. The at least one predetermined imaging volume may include a large three-dimensional imaging volume for generating a scout image which estimates a three-dimensional center of the heart and the general size of the heart. The at least one predetermined imaging volume may include a small three-dimensional imaging volume for generating SPECT images of the heart. The combination of the location of spaced longitudinal slits, the angle of the slit-guides, and the distance between the slit-plate and the detector subsystem may be adjusted for minification of a plurality of simultaneous non-overlapping projections cast on the detection system to provide high geometric efficiency for generating one or more SPECT images. The one or more SPECT images may be obtained by using image reconstruction of the plurality of simultaneous non-overlapping projections. The collimator subsystem may include a plurality of transversely spaced slats disposed behind the slit-plate for longitudinally collimating the radiation photons. The location of each of the plurality of transversely spaced slats may be configured to adjust spatial resolution of longitudinal collimation. The transversely spaced slats may be configured to converge on predetermined focal points of a cone-beam of radiation photons emitted from the heart for increasing the number of radiation photons detected by the detector subsystem. The slit-plate may be configured as a flexible loop moveably coupled to the frame having a plurality of sections each configured to provide a unique predetermined imaging volume having a predetermined size and location, and a spatial resolution. The desired section of the flexible loop may be positioned proximate and surrounding the at least one predetermined imaging volume of the patient by driving the flexible loop to a predetermined location on the collimator subsystem. The system may include a plurality of connected flexible loops moveably coupled to the frame, each loop including a plurality of sections configured to provide a unique predetermined imaging volume of a predetermined size, location, and spatial resolution. The system may include a patient positioning subsystem for positioning the patient such that the heart is located proximate the center of the predetermined imaging volume based on previous scout images of the heart. The patient positioning subsystem may incrementally rotate the patient about a central longitudinal axis of the at least one predetermined imaging volume for obtaining a plurality of images. The patient positioning subsystem may intermittently and incrementally rotate the patient about a predefined central longitudinal axis of a small predetermined three-dimensional imaging volume for obtaining a plurality of sequentially acquired sets of simultaneous projections and reconstructing a one or more SPECT images. The patient positioning subsystem may position the patient at predetermined locations of the central longitudinal axis to position the predetermined imaging volume at the appropriate position to increase sensitivity and improve image quality. A patient positioning subsystem may position the predefined imaging volume encompassing the heart up and down about a longitudinal axis for acquiring additional imaging data in a longitudinal plane. The system may include a source of radiation for emitting a beam of radiation photons towards and encompassing the three-dimensional imaging volume and the thorax of the patient. The collimator system may include a plurality of vertical slats configured to define a plurality of longitudinal slits of a predetermined width for transversely collimating the beam of radiation photons. The plurality of longitudinal slits may have non-uniform widths for focusing on the source of radiation and optimizing collimation of the radiation photons emitted from the source of radiation. The vertical slats may be configured to aim at the source of radiation. The collimator subsystem may include a plurality of transversely spaced parallel slats disposed behind the vertical slats for longitudinally collimating the beam of radiation photons. The distance between each of the plurality of transversely spaced slats may be configured to adjust spatial resolution of longitudinal collimation. The source of radiation photons may include a line source for emitting a three-dimensional fan beam of radiation photons which encompasses the three-dimensional imaging volume. The source of radiation may include a longitudinal scanning point source configured to emit a three-dimensional fan beam of radiation photons which encompasses the three-dimensional imaging volume. The source of radiation photons may include a point source for emitting a three-dimensional cone beam of radiation photons which encompasses the three-dimensional imaging volume. The collimator subsystem may include a plurality of transversely spaced slats converging on a predetermined focal point of the point source for collimating the cone beam of radiation photons and for increasing the amount of radiation photons detected by the detector subsystem. The distance between each of the plurality of spaced converging slats may be configured to adjust the spatial resolution of longitudinal collimation. The point source may include an x-ray tube.

This invention also features an integrated single photon emission computed tomography (SPECT)/transmission computed tomography (TCT) system for cardiac imaging including an open arc-shaped frame, a collimator system is shaped to approximately match the thoracic contour of patients having different sizes and weights and shaped to surround and position the collimator closely proximate a heart of a patient of said patients encompassed by at least one predetermined image volume for optimizing collimation of radiation photons emitted from the heart. An arc-shaped detector system is coupled to the collimator subsystem having a shape closely matching the shape of the collimator subsystem for detecting collimated radiation photons from the collimator subsystem and generating output electrical signals. A patient positioning system positions a patient to and about a predetermined central longitudinal axis of a three-dimensional imaging volume of the patient, a movable source of radiation emits a beam of radiation photons to and encompassing the three-dimensional imaging volume, and wherein the movable point source is rotated in one direction about the central longitudinal axis and the patient is rotated in an opposite direction about the central longitudinal axis for generating a plurality of TCT images.

This invention further features an integrated single photon emission computed tomography (SPECT)/transmission computed tomography (TCT) system for cardiac imaging including an open arc-shaped frame, a collimator system is shaped to approximately match the thoracic contour of patients having different sizes and weights and shaped to surround and position the collimator closely proximate a heart of a patient of said patients encompassed by at least one predetermined image volume for optimizing collimation of radiation photons emitted from the heart, the collimator subsystem further including plurality of transversely spaced slats converging on a predetermined focal point of an x-ray source emitting a three-dimensional cone beam of radiation photons which encompasses the three-dimensional imaging volume for optimizing collimation of the cone beam of radiation photons. An arc-shaped detector system is coupled to the collimator subsystem having a shape closely matching the shape of the collimator subsystem for detecting collimated radiation photons from the collimator subsystem and generating output electrical signals. A patient positioning subsystem positions a patient to a predetermined central longitudinal axis of the three-dimensional imaging volume and for intermittently and incrementally rotating the patient about the predetermined central longitudinal axis for generating a plurality of TCT images.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
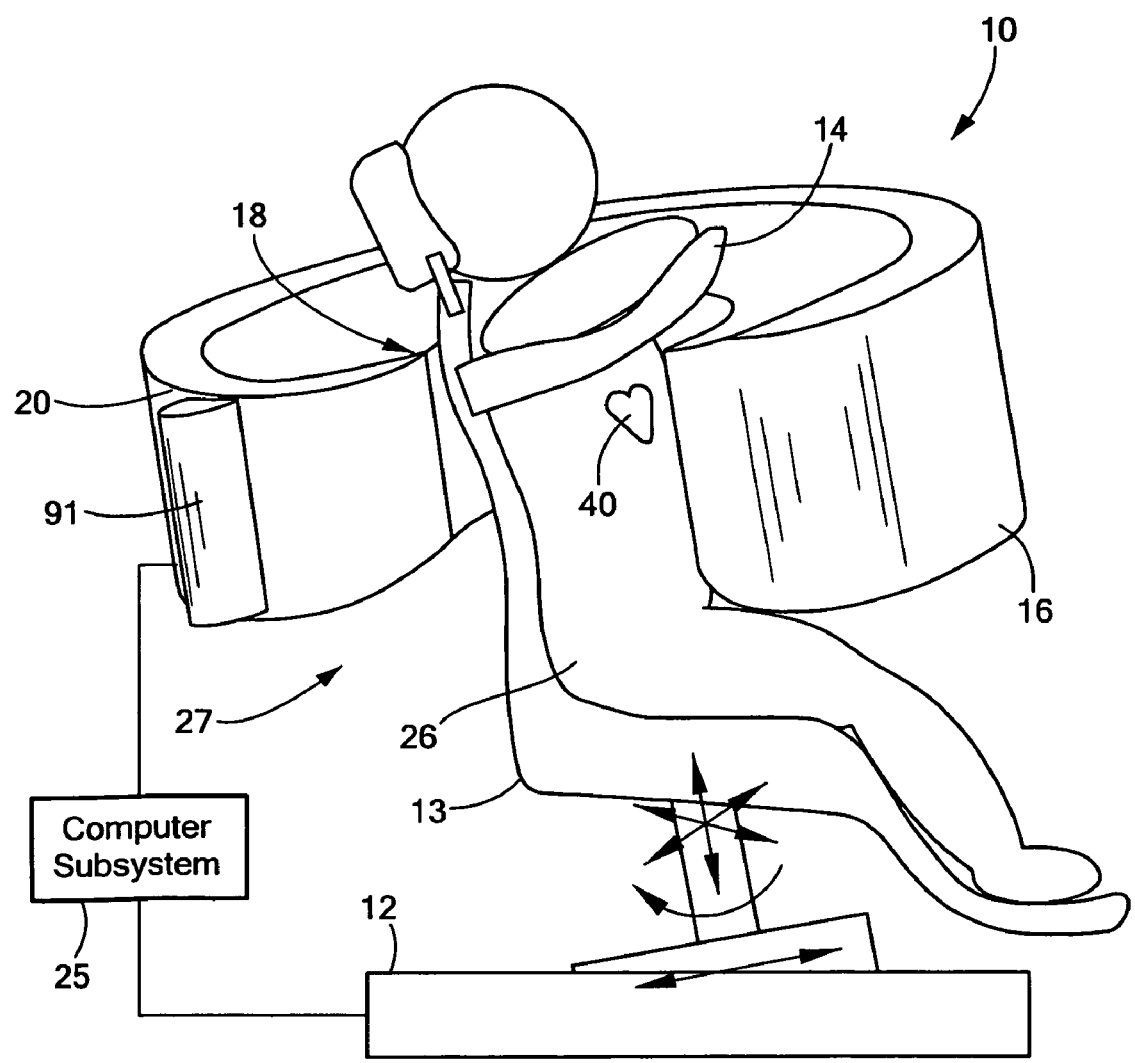
FIG. 1 is a three-dimensional side view of one embodiment of the hybrid SPECT/TCT system for cardiac imaging of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
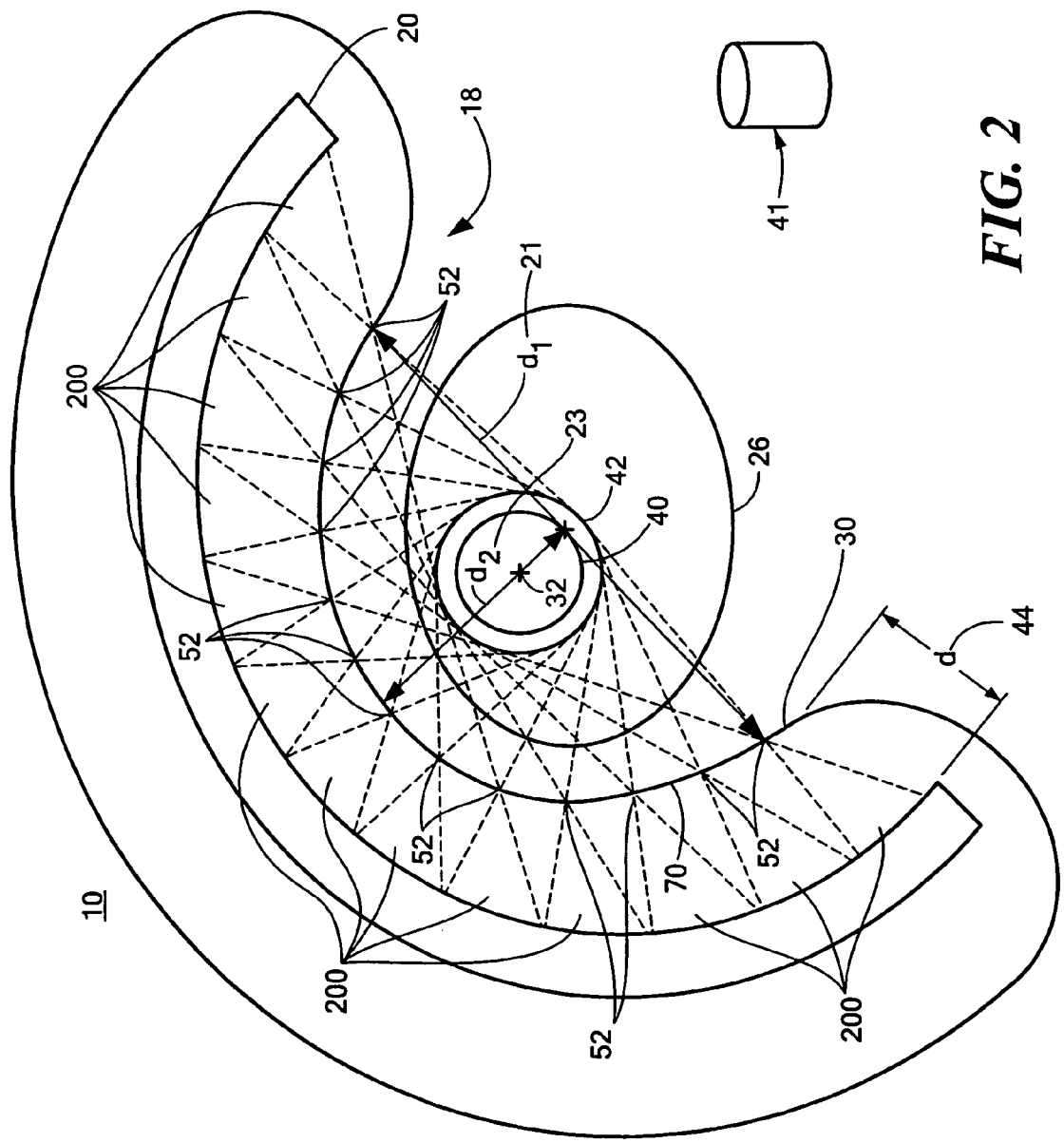
FIG. 2 is a schematic top view of one embodiment of the hybrid SPECT/TCT system for cardiac imaging of this invention configured for a predetermined imaging volume (PIV) of a typical sized patient.
Figure 3:
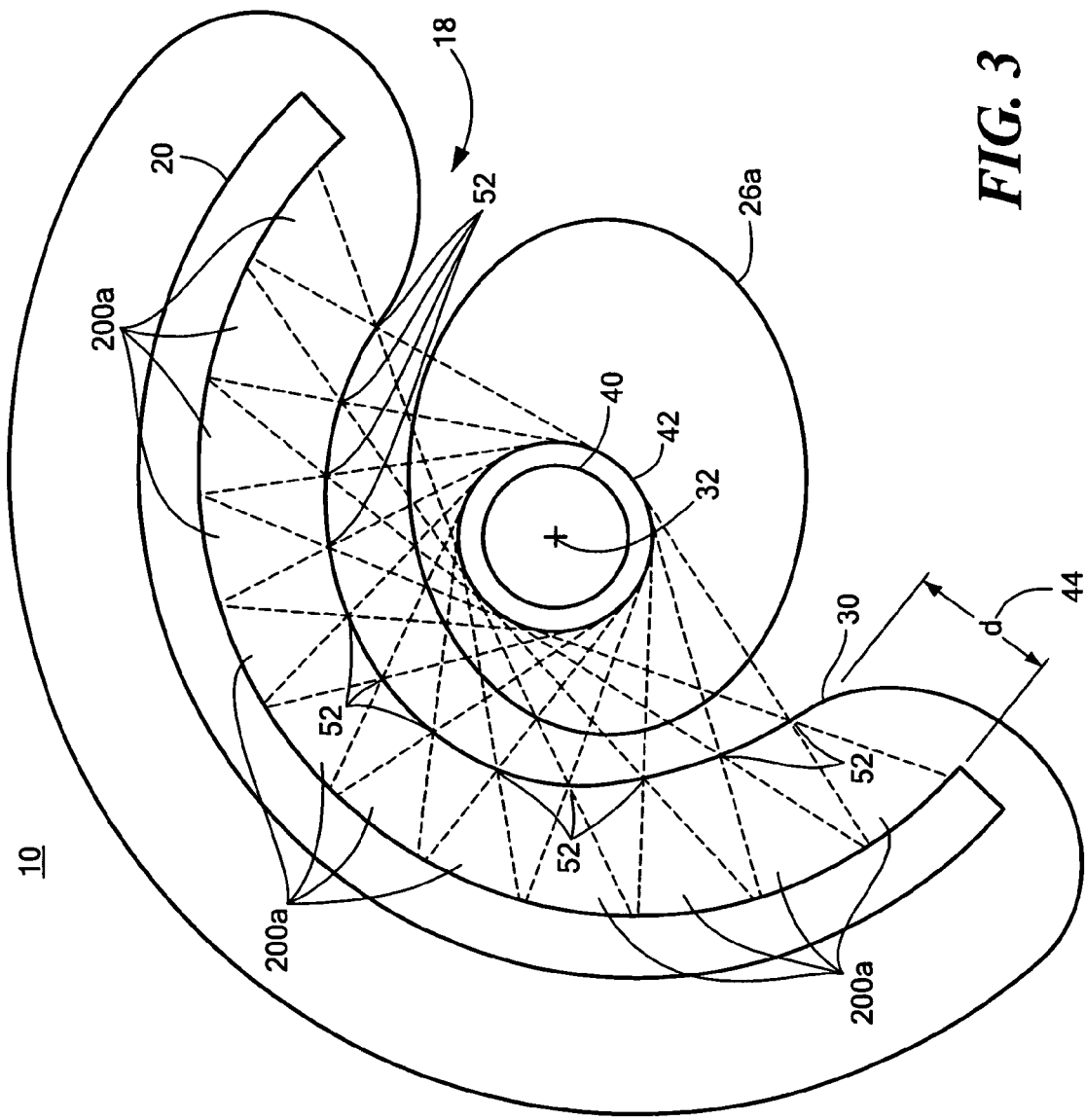
FIG. 3 is a schematic top view one embodiment of the hybrid SPECT/TCT system for cardiac imaging of this invention configured for PIV of a large patient.

There is shown in FIG. 1, one embodiment of integrated SPECT/TCT system 10 of this invention. System 10 includes collimator subsystem 18 coupled to frame 16, which is shaped to an open-arc to approximately match the thoracic contour of patient 26, as better shown, e.g., in FIGS. 2 and 3. Collimator subsystem 18, FIGS. 1-3, is fairly large and has a cross-section, e.g., about 55 cm, as shown at $d_1$-21, FIG. 2, and about 25 cm as shown at $d_2$-23, or any equivalent dimensions as known by those skilled in the art. Collimator subsystem 18, FIGS. 2-3, is responsive to radiation photons emitted from heart 40, e.g., the circle representing the heart of patient 26, as shown in FIG. 1. As discussed in the Background section above, radiation photons emit from heart 40 as a result from ingestion or intravenous injection of a radiopharmaceutical. The shape of collimator subsystem 18, FIGS. 1-3, is designed to approximately the thoracic contour of patient 26. This allows collimator subsystem 18 to be closely proximate to heart 40 to optimize collimation of radiation photons from heart 40 encompassed by at least one PIV, e.g., PIV 42, FIG. 2, of a typical sized patient 26, or PIV 42a, FIG. 3, of a larger sized patient. The shape of open-arc collimator subsystem 18, FIGS. 1-3, is also designed to accommodate data sampling for the off-center location of heart 40. The result is collimator subsystem 18 effectively collimates radiation photons from heart 40 of the majority of the patients in a typical patient population. Collimator subsystem 18 may be oval shaped, elliptical shaped, hyperbolic shaped, a composite of the aforementioned shapes, or any shape known to those skilled in the art which will result in collimator subsystem 18 approximately matching the thoracic contour of patient 26 and being located closely proximate heart 40 encompassed by PIV 42, FIG. 2, or PIV 42a, FIG. 3.

Detector subsystem 20, FIGS. 2 and 3, is located behind collimator subsystem and has a shape which closely matches the shape of collimator subsystem 18, as discussed above. Detector subsystem 20 is responsive to collimator subsystem 18 and detects collimated radiation photons emitted by heart 40 and generates output electrical signals. Detector subsystem 20 preferably includes a plurality of closely spaced detector modules 72, FIGS. 4 and 5 that maximize packing fraction and detection efficiency while providing high intrinsic spatial resolution (ISR). Detector modules 72 could be made from a variety of radiation detector material, such as scintillation detectors or room-temperature solid-state detectors. Detector modules 72 may be solid-state CZT detectors or advanced pixellated scintillation detectors, as known by those skilled in the art. Computer system 25, FIG. 1, receives digitized output electrical signals from the plurality of detectors and its associated electronics processing subsystem and generates one or more raw projection images of the heart.

Preferably arc-shaped frame 16, FIGS. 1-3, collimator subsystem 18, and detector subsystem 20 are subtended at an angle in the range of about 180° to 220° with respect to center 32 of heart 40.

Figure 4:
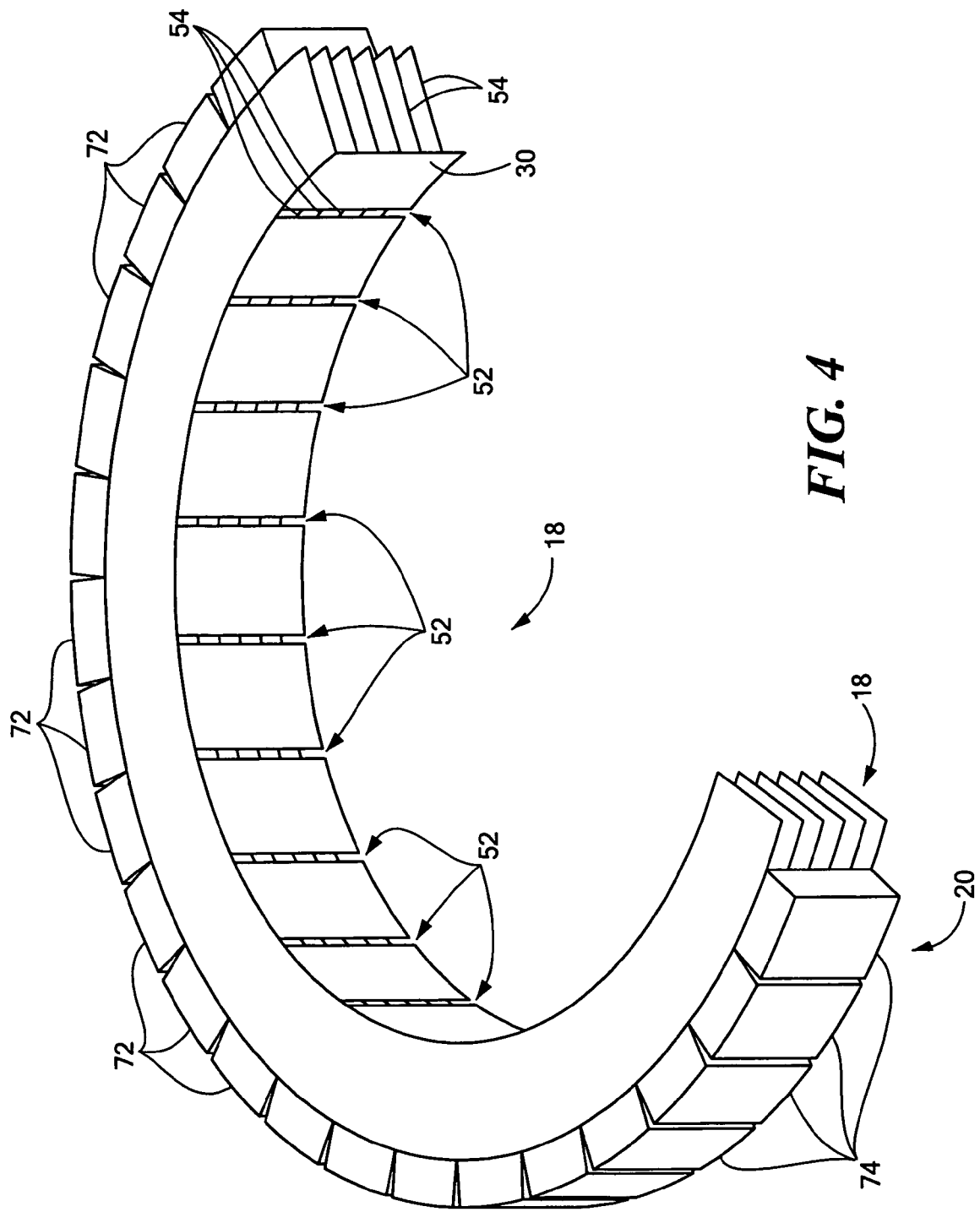
FIG. 4 is a three-dimensional view of a one embodiment of the collimator subsystem and the detector subsystem of this invention shown in FIGS. 1-3 used for high quality SPECT images of the heart.

In one design, collimator subsystem 18, FIGS. 2 and 3, includes slit-plate 30 having a predetermined number of spaced longitudinal slits 52 of a predetermined width. In this example, each slit 52 in slit-plate 30 has a predetermined width of about, e.g., 2 to 5 mm, as shown in FIG. 4. Slits 52 transversely collimate the radiation photons emitted from heart 40 encompassed by PIV 42, FIG. 2, or PIV 42a, FIG. 3. Each slit 52 functions as a ID pinhole in the transverse plane casting a plurality of projections 200, FIG. 2, or a plurality of projections 200a, FIG. 3, of radiation photons emitted from PIV 42, or PIV 42a, respectively, onto detector subsystem 20.

Figure 5:
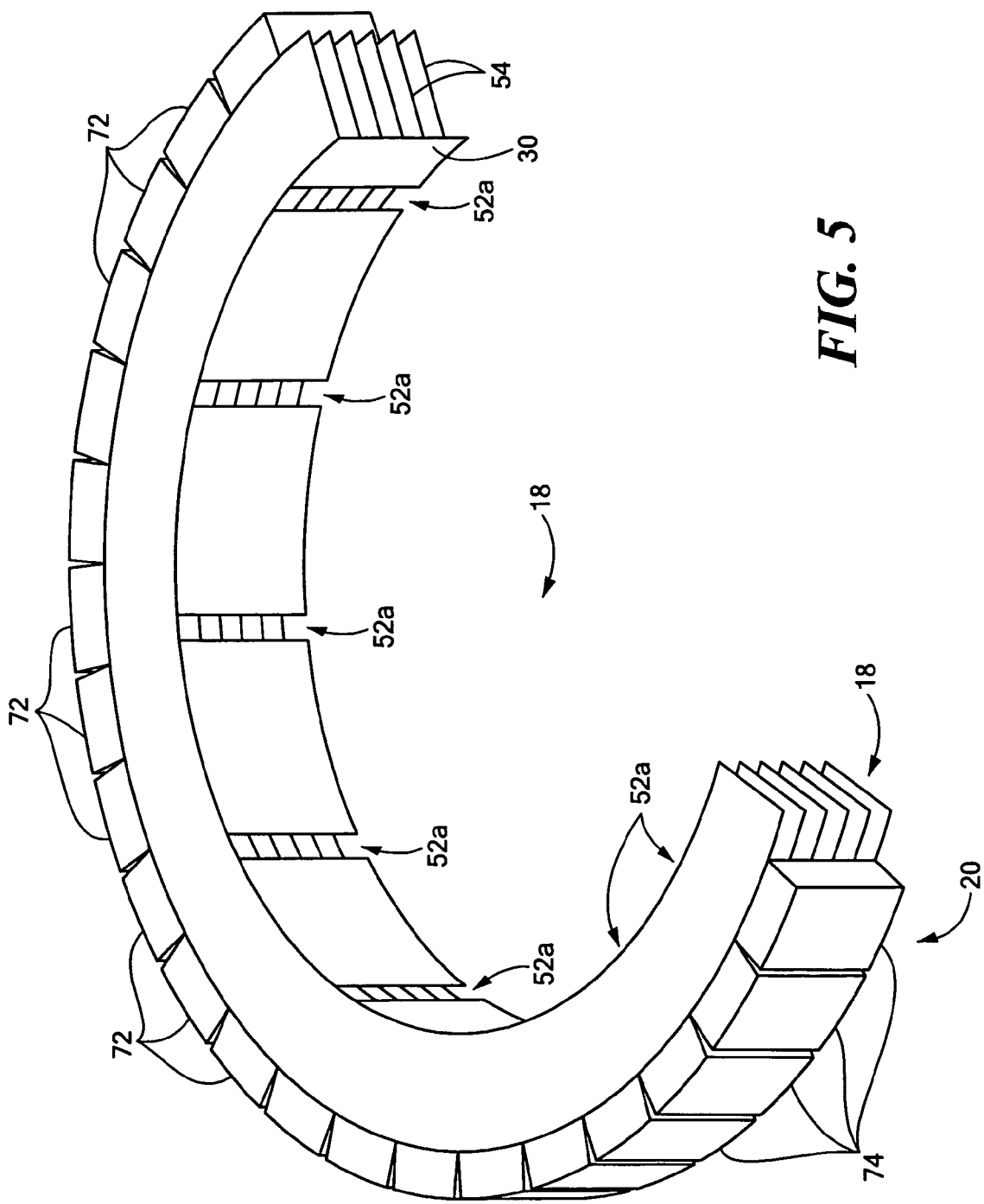
FIG. 5 is a three-dimensional view of another embodiment of the collimator subsystem and the detector subsystem of this invention shown in FIG. 1-3 used for obtaining scout images.

In another design, collimator subsystem 18, FIG. 5, includes a predetermined number of spaced wider slits 52a, e.g., about 5 to 8 slits 52a, having a predetermined wider width of about, e.g., about 8-12 mm.

The width of each of longitudinal slits 52, and slits 52a, FIGS. 2-5, is configured to adjust spatial resolution and photon sensitivity of transverse collimation of the radiation photons emitted from the heart 40. Wider slits, e.g., slits 52a, FIG. 5, provide generally lower spatial resolution but are more sensitive, e.g., for use with scout imaging. Narrower slits, e.g. slits 52, FIG. 2-4, provide generally higher spatial resolution but are less sensitive, e.g., for the construction of more accurate SPECT images of the PIV 42, FIG. 2 or PIV 42a, FIG. 3, with heart 40 therein.

Figure 6:
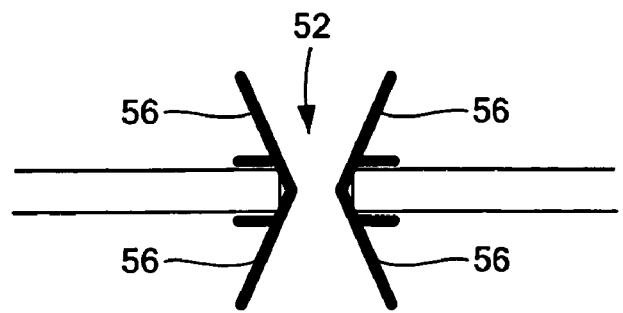
FIG. 6 is a schematic side view showing a one embodiment of slit-guides disposed on each side of the longitudinal slits shown in FIGS. 2-5.

In one preferred embodiment of this invention, collimator subsystem 18, FIGS. 1-5, includes slit-guides 56, FIG. 6, attached proximate each side of each of spaced longitudinal slits 52, 52a. In one example, slit-guides 56 are made of lead or similar type radiation-opaque material. The angle $\theta_1$-55, FIG. 7, of slit-guides 56, and the angle $\theta_2$-57, of slit-guides 56 with respect to axis 59 and the spacing between slits 52, 52a, FIGS. 2-5, are configured to define, inter alia, the size and location of PIV 42, FIG. 2, for a typical sized patient 26, PIV 42a, FIG. 3, for a larger patient 26, and a large PIV 42b, FIG. 8, for scout imaging. The combination of the angle of the slit-guides 56 and the spacing between slits 52, 52a provides the flexibility to define multiple PIVs at predetermined locations needed for patients having different thoracic contours, weights, and different sized hearts located further from central longitudinal axis 32 than a typical patient 26. The precisely targeted and optimized design and selection of PIVs 42, 42a, and 42b, results in high quality SPECT imaging and improved scout images.

Figure 7:
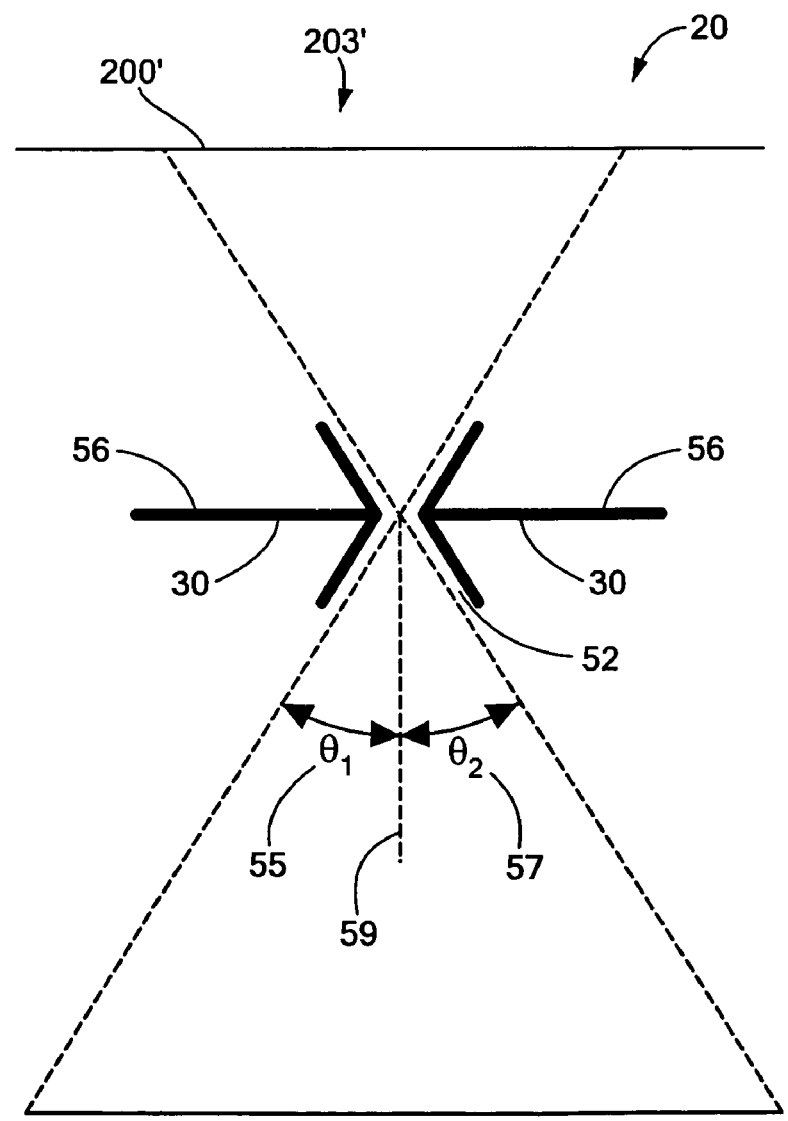
FIG. 7 is a schematic side view showing in further detail the angle of the slit-guide shown in FIG. 6.
Figure 8:
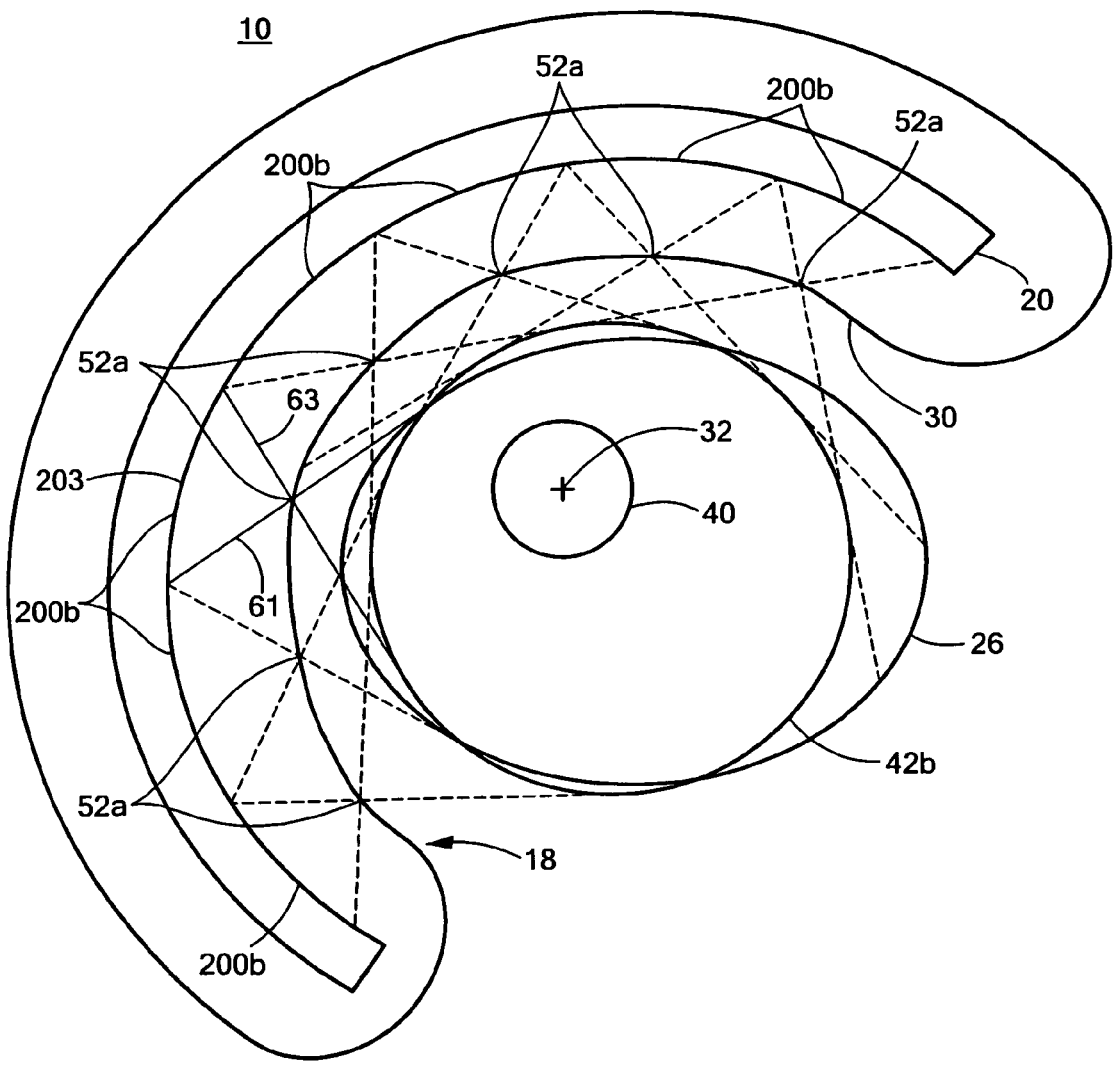
FIG. 8 is a schematic top view of another embodiment of the hybrid SPECT/TCT system for cardiac imaging of this invention configured for a PIV used for scout imaging.
Figure 9:
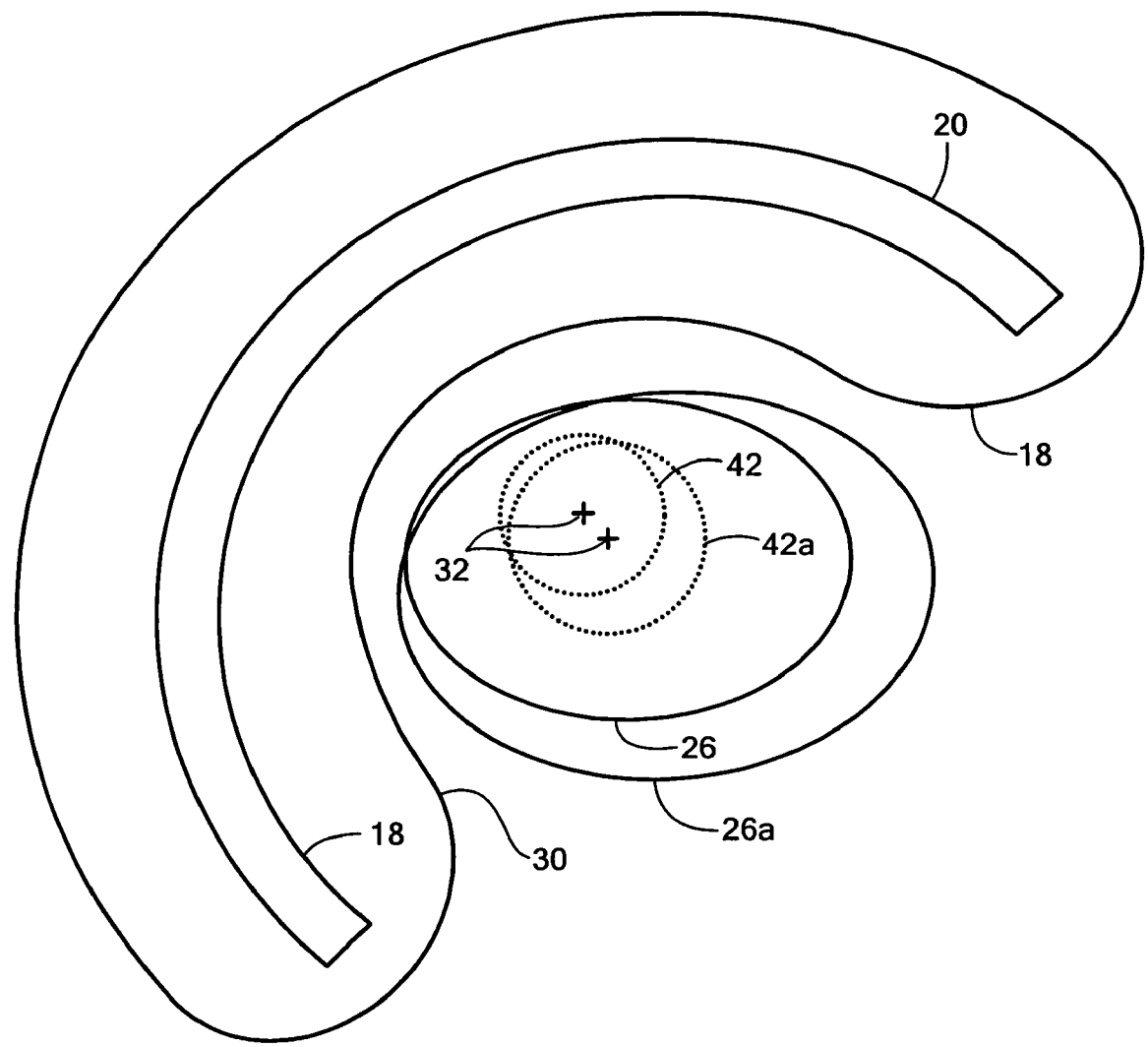
FIG. 9 is a schematic top view showing a comparison of the PIVs and patients shown in FIGS. 2 and 3.

For example, the angle $\theta_1$-55 and $\theta_2$-57, FIG. 7, with respect to axis 59, of slit-guides 56 and the spacing between slits 52, FIG. 2, defines a plurality of non-overlapping projections 200 which are cast on detector subsystem 20 to define PIV 42 for typical sized patient 26. Similarly, the combination of the angle $\theta_1$-55 and $\theta_2$-57, of the slit-guides 56, FIG. 7, and the spacing between slits 52, FIG. 3, defines a plurality of non-overlapping projections 200a, FIG. 3 which are cast on detector subsystem 20 to define PIV 42a of a larger sized patient 26a having a heart 40 which is larger and located further from central longitudinal axis 32 than a typical patient 26. FIG. 9, where like parts have been given like numbers, shows a comparison of PIV 42 of patient 26 and PIV 42a of larger patient 26a, as shown in FIGS. 2 and 3, respectively. Additionally, the combination of the angle $\theta_1$-55 and $\theta_2$-57 with respect of axis 59, FIG. 7, and the spacing between longitudinal slits 52a, FIG. 8, can also be configured to define a plurality of non-overlapping projections 200b which are cast on detector subsystem 20 to define a much larger PIV 42b, in the thoracic cross-section of patient 26 that covers heart 40 for generating a series of scout images to locate the center of heart 40. In this example, slit-plate 30 of collimator subsystem 18 may include about 5 to 8, e.g., 7 longitudinal slits 52a, as better shown in FIG. 5, each having a width of about 10 mm. Lines 61 and 63, FIG. 8, show two exemplary peripheral paths of radiation photons emitted from large PIV 42b and cast on detector subsystem 20 to create one of the plurality of projections 200b, indicated at 203. Center 32 and the longitudinal central axis that passes through center 32 of the heart 40 can be estimated either by inspecting raw projections of scout images or by real-time tomographic reconstruction of the plurality of raw projections 200b cast on the detector subsystem 20 to derive three-dimensional scout SPECT images. Thus, the wider width of the slits 52a provides quick, low-resolution images of the large PIV 42b for scout SPECT imaging.

The result is integrated SPECT/TCT system 10 for cardiac imaging of this invention provides multiple PIVs at multiple locations needed for high quality SPECT images of heart 40 for both typical and large sized patients having different thoracic contours, weights, and different sized hearts located further from central longitudinal axis 32 than a typical patient 26.

Because the collimator subsystem 18, FIGS. 1-5, 8 and 9, is not circular, slits 52, 52a are not evenly spaced angularly with respect to the center of PIV 42, FIG. 2, PIV 42a, FIG. 3, or PIV 42b, FIG. 8. This unevenness in angular sampling requires computer subsystem 25, FIG. 1 to utilize iterative algorithms, such as Ordered Subset-Expectation Maximization (OS-EM), for tomographic image reconstruction.

Collimator subsystem 18, FIGS. 1-5, 8 and 9, preferably includes a plurality of transversely spaced slats 54, as shown in FIGS. 4 and 5, disposed behind slit-plate 30. Slats 54 longitudinally collimate the radiation photons. In one example, the distance between each of the plurality of transversely spaced slats 54 is configured to adjust spatial resolution of longitudinal collimation. Slats 54 are typically multiple thin parallel lead plates or foils, and may be separated with styrofoam plates (not shown) of uniform thickness, e.g., about 2-5 mm. Slats 54 basically fill the space (with varied radial length, e.g., 50-100 mm), between the two ends of collimator subsystem 18 and between collimator subsystem 18 and detector subsystem 20.

Figure 10:
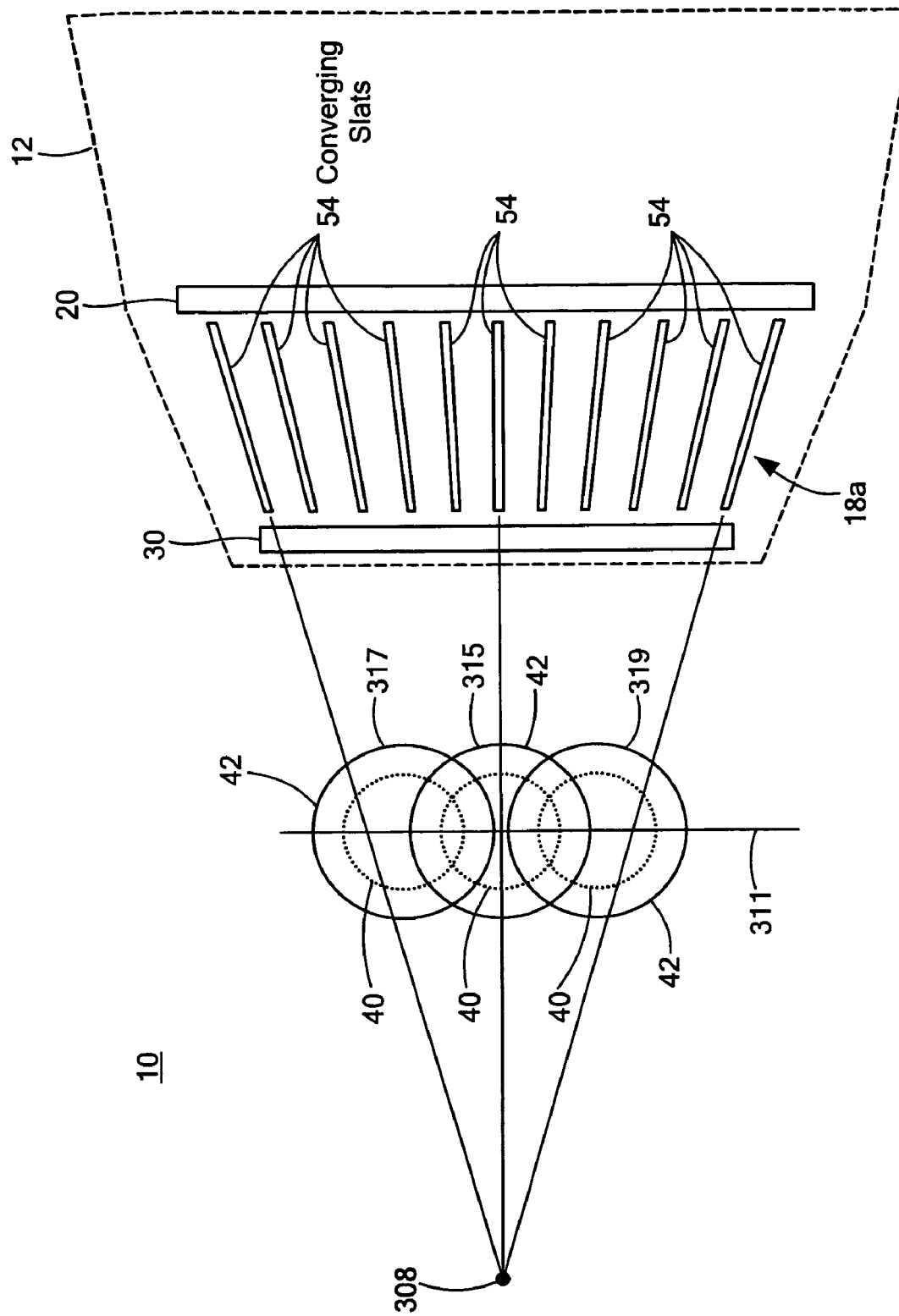
FIG. 10 is a schematic side view of one embodiment of the hybrid SPECT/TCT system for cardiac imaging having a collimator subsystem with converging slats.

In one embodiment, integrated SPECT/TCT system 10, FIG. 10, shown in a longitudinal plane, includes collimator subsystem 18a having a plurality of transversely-spaced slats 54 which converge on predetermined focal points, shown in two dimensions as point 308. In this embodiment, collimator subsystem 18a of system 10 utilizes a variation of conventional cone-beam geometry (which relies on a collimator design with a plurality of pin holes which are all aligned in three-dimension to a single point beyond the target organ, such as the brain) for each slit of collimator subsystem 18, e.g., slits 52, FIGS. 2-3, for PIV 42, 42a, respectively. The advantage of using converging-slats 54 is the increased solid angle for photon detection, and corresponding increased geometric sensitivity. Appropriate cone-beam algorithms are applied in image reconstruction. However, since cone-beam sampling may have limitations in providing artifact-free 3D images, mainly in the upper and lower regions of the cone-beam, a few additional longitudinal sampling could be utilized to reduce these artifacts and provide satisfactory images. In this example, patient positioning subsystem, FIG. 1, moves patient 26 up and down along longitudinal axis 311 to acquire more imaging data from the radiation photons emitted from heart 40 encompassed by PIV 42 in the longitudinal plane. In this example, PIV 42 (or PIV 42a, FIG. 3) encompassing heart 40 is sampled three times at positions 317, 315, and 319. Using converging-slats 54 increases the solid angle of radiation photons received by detector subsystem 20 and increases detection efficiency by detector subsystem 20. The result is high speed or high quality SPECT imaging of heart 40.

Figure 11:
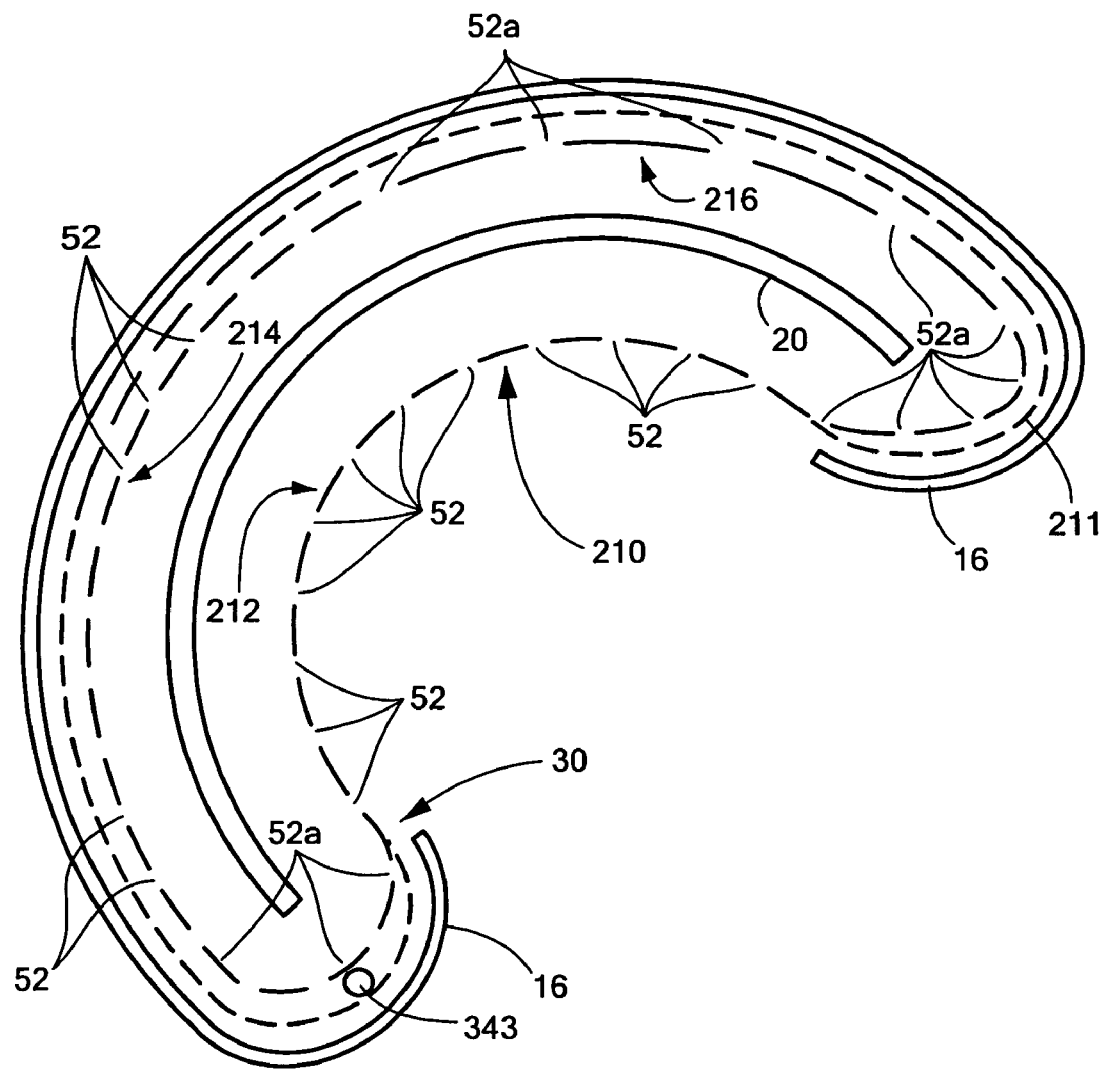
FIG. 11 is a schematic top view of one embodiment of the hybrid SPECT/TCT system for cardiac imaging of this invention including a movable loop having a plurality of sections for defining multiple PIVs.

In one preferred design, slit-plate 30, FIGS. 2-5, 8 and 9, is configured as movable loop 210, FIG. 11. Loop 210 is slideably coupled to frame 16. Movable loop 210 includes a plurality of sections, e.g., section 212, section 214, and section 216. Each of sections 212, 214 and 216 include a predefined number of spaced longitudinal slits 52, 52a, each having slit-guides 56 proximate each side thereof at a predetermine angle and each having a predetermined width to define PIV 42, FIG. 2, PIV 42a, FIG. 3, and PIV 42b, FIG. 8, respectively, as discussed above. In this example, section 212 is shown located at the front of collimator subsystem 18.

Figure 12:
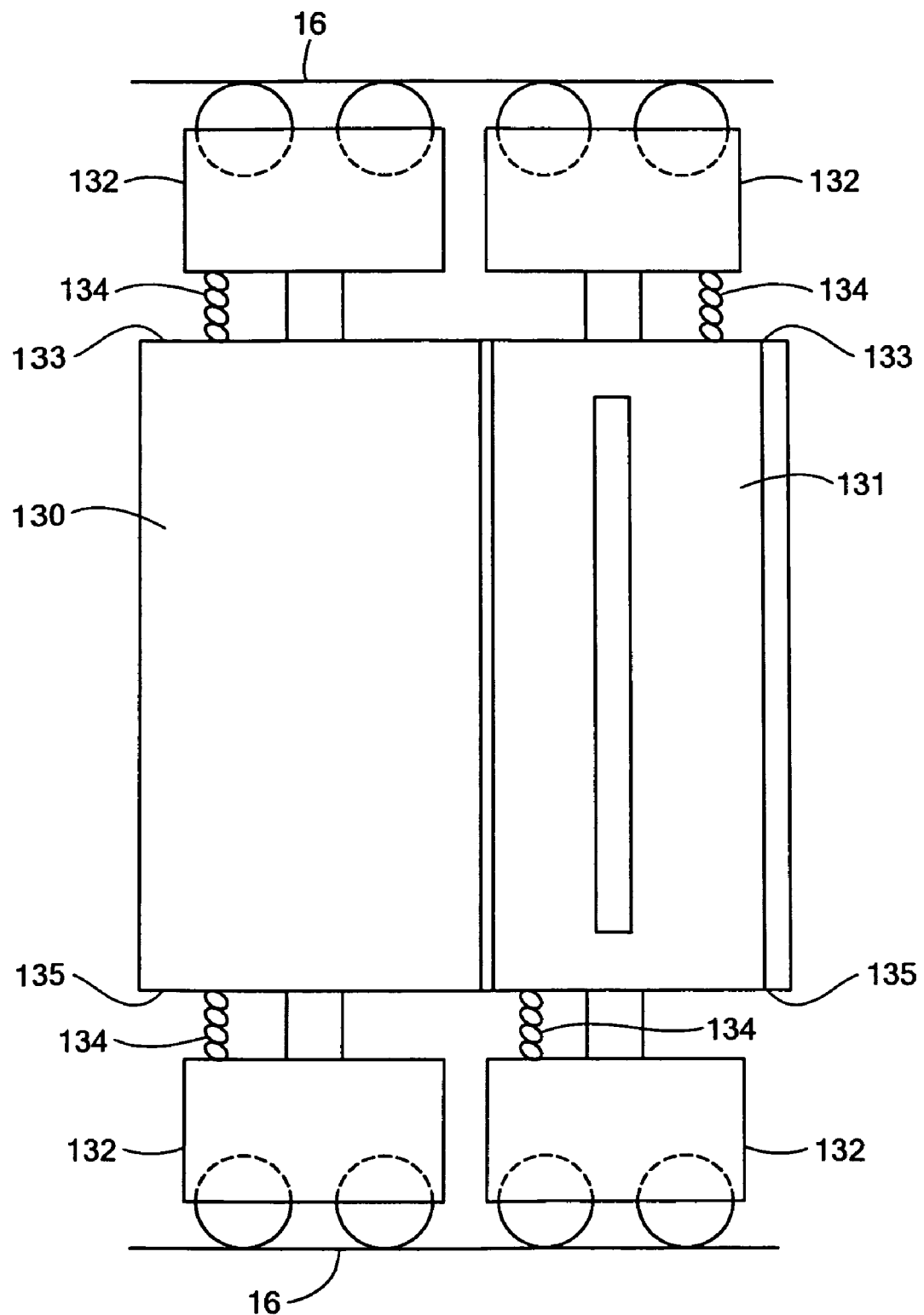
FIG. 12 is a schematic top view showing one example of two collimator segments of a section of the loop shown in FIG. 11.
Figure 13:
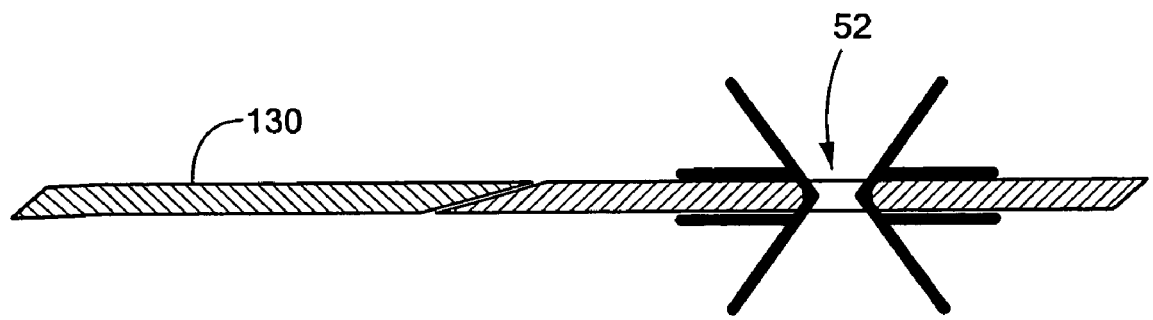
FIG. 13 is a schematic front view showing in further detail the structure of the segments shown in FIG. 12.

Each of sections 212-216 of each section is preferably coupled to movable cars 132, FIG. 12. For example, section 212 includes a plurality of segments 130 and 131, as shown in greater detail in FIG. 13, which are coupled on top surface 133, FIG. 12, to cars 132 movably coupled to frame 16 and coupled on bottom surface 135 to movable cars 132 coupled the frame 16. In one design, biasing devices 134, e.g., springs, disposed between cars 132 and segments 130 and 131 maintains segments 130 and 131 in an appropriate and reproducible position for imaging. In an exemplary embodiment, stepper-motor 343, FIG. 11, controlled by computer subsystem 25, FIG. 1, drives cars 132, FIG. 12, on tracks (not shown) in frame 16 so that the desired section of loop 210, FIG. 11, is located at the front of collimator subsystem 18 for imaging.

In one design, collimator subsystem 18, FIG. 11 includes a plurality of connected loops, e.g., loop 210 and loop 211 that each including a plurality of sections and share a common section, e.g., section 210 disposed proximate patient 26. As discussed above, each of the connected loops 210 and 211 are slideably coupled to frame 16. A switching system may be used to select the track of choice and allow a specific section to be pulled to the front. The track flexibilities and functionalities are available from well-developed track technology.

The result is integrated SPECT/TCT system 10 for cardiac imaging, FIGS. 1-13 of this invention, can select a desired PIV 42, FIG. 2, PIV 42a, FIG. 3, or PIV 42b, FIG. 8, as needed for different sized patients and for scout imaging by simply moving the desired section 212-214, FIG. 11, to the front of collimator subsystem 18 to provide scout images and high quality SPECT images of the heart.

In one embodiment of this invention, the distance, d, indicated at 44, FIGS. 2 and 3, between slit-plate 30 of collimator subsystem 18 and detector subsystem 20 is configured for minification of the plurality of simultaneous non-overlapping projections 200, 200a on the detector subsystem 20. To accommodate the large number of plurality of projections 200, 200a, on detector subsystem 20, each projection needs to be small enough so that there is no overlap of adjacent projections, 200, 200a on detector subsystem 20. This is achieved through minification of the plurality of projections 200, 200a by adjusting distance d-44 at the appropriately the distance between the slit-plate 30 and detector subsystem 20, e.g., to a distance of about 5-10 cm and by adjusting the angle of plurality of slit-guides 56, FIGS. 6 and 7, e.g. $\theta_1$-55 and $\theta_2$-57 with respect to axis 59. The angle of slit-guides 56 limits the radiation photons only from PIV 42, FIG. 2, or PIV 42a, FIG. 3. This design allows a large number of non-overlapping projections to be acquired simultaneously and thus provides high geometric efficiency in detection of the radiation photons emitted from PIV 42 or PIV 42a, used or SPECT imaging of heart 40.

In one design of this invention, patient positioning subsystem 12, FIG. 1, positions patient 26 to one or more predetermined locations defined by PIV 42, FIG. 2, PIV 42a, FIG. 3, or PIV 42b, FIG. 8, so that patient 26 can be rotated on a central axis of the appropriate PIV which contains the heart 40 throughout the whole series of rotation for SPECT imaging (discussed in detail below). Patient positioning subsystem 12, FIG. 1, may include chair 13 that is incrementally rotated to obtain a plurality of projection images. The longitudinal axis of the frame 16 may be oriented nearly, but not exactly, vertically such that the patient 26 sits nearly upright. More realistically, patient 26 should sit in a slightly reclined bucket seat, with his back firmly supported so that patient 26 feels comfortable, with low likelihood of torso movement, to go through the imaging procedure. This arrangement facilitates rotation of patient 26 during imaging and allows a small footprint of the system 10. Upright imaging provides the advantage of lowering the diaphragm of the patient 26, thus reducing the severity of attenuation and scatter effects caused by sub-diaphragmatic organs and sub-diaphragmatic tracer accumulations.

Patient positioning subsystem 12, FIG. 1, positions patient 26 so that the center of the heart 40 is at center 32, FIGS. 2 and 3, of the three-dimensional field PIV 42 or PIV 42*a* based on a previous scout imaging of the heart. However, a single set of plurality of 12-20 projections is typically not enough for reconstructing high quality SPECT images of heart 40. Thus, several (2-5) additional sets of non-redundant projections may be acquired, depending on image quality requirements of the specific clinical application. These additional sets of non-redundant projections can be added by rotating patient 26 on the positioning subsystem 12, FIG. 1, relative to the other hardware, to sample slightly different projections. Patient positioning subsystem 12, then incrementally rotates patient 26, e.g., approximately 3° for a total of 12° to 15° to fill in the angular sampling gaps about a predefined central longitudinal axis, e.g., center 32 of PIV 42, FIG. 2 or center 32, FIG. 3 of PIV 42*a*, and then intermittently remains stationary, e.g., for about 30-120 seconds to obtain additional plurality of ECT projections 200, FIG. 2 or a plurality of projections 200*a*, FIG. 3. Frame 16, collimator subsystem 18 and detector subsystem 20 remain stationary at all times. Computer subsystem 25, FIG. 1, reconstructs SPECT images from the whole sets of the plurality of ECT projections 200, FIG. 2, or the plurality of projections 200*a*, FIG. 3.

For proper correction of these pre-corrected SPECT images, the third phase—TCT imaging—is an integral part of the process. In order to obtain TCT images, patient positioning subsystem 12, FIG. 1 positions patient 26 to a different central longitudinal axis of a larger three-dimensional PIV, e.g., a central longitudinal axis that passes through center 38, FIG. 14 of a larger three-dimensional PIV 42*c*, FIG. 15, of patient 26.

Figure 15:
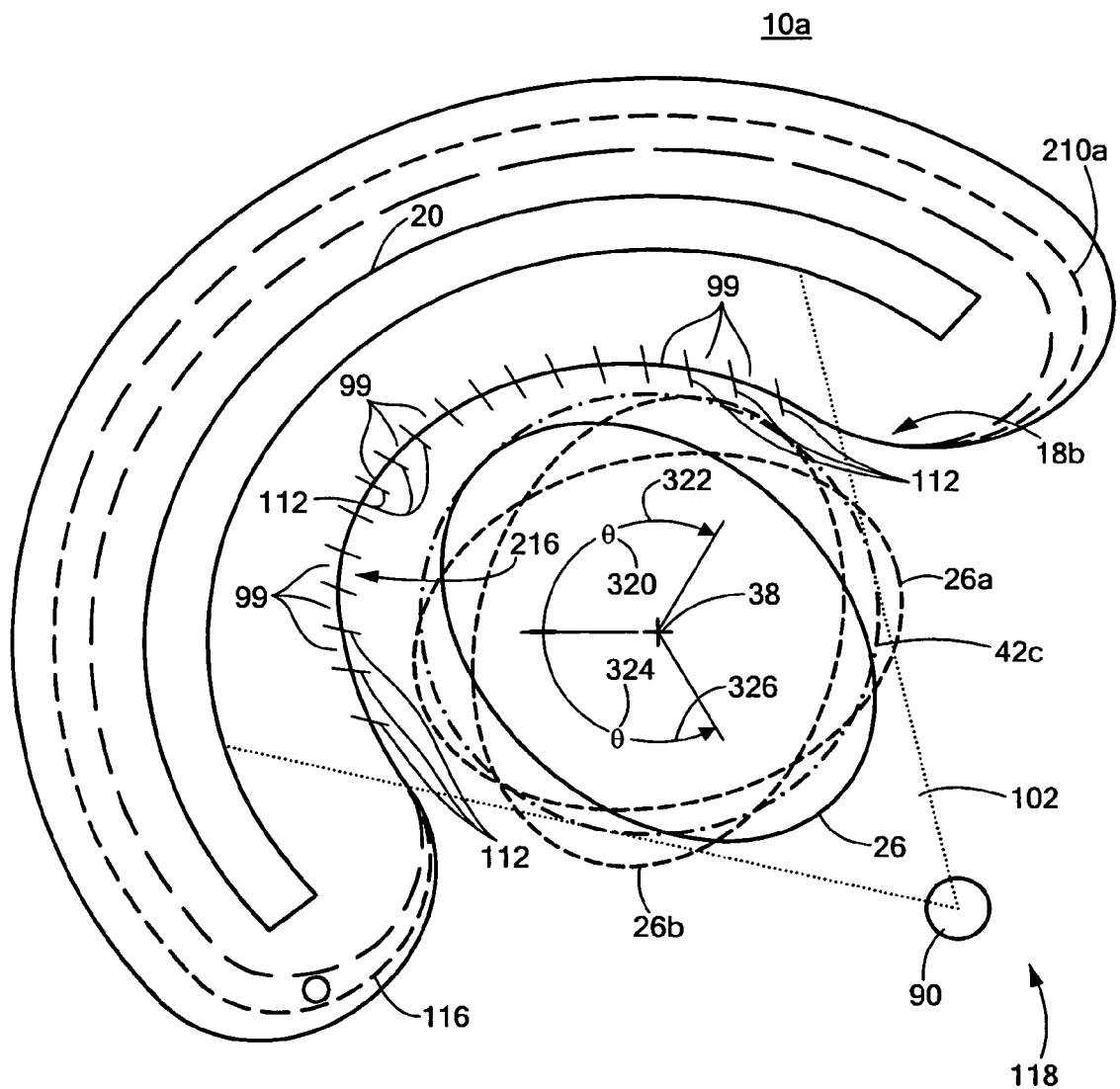
FIG. 15 is a schematic top view of another embodiment of the SPECT/TCT system of this invention used for TCT imaging.
Figure 16:
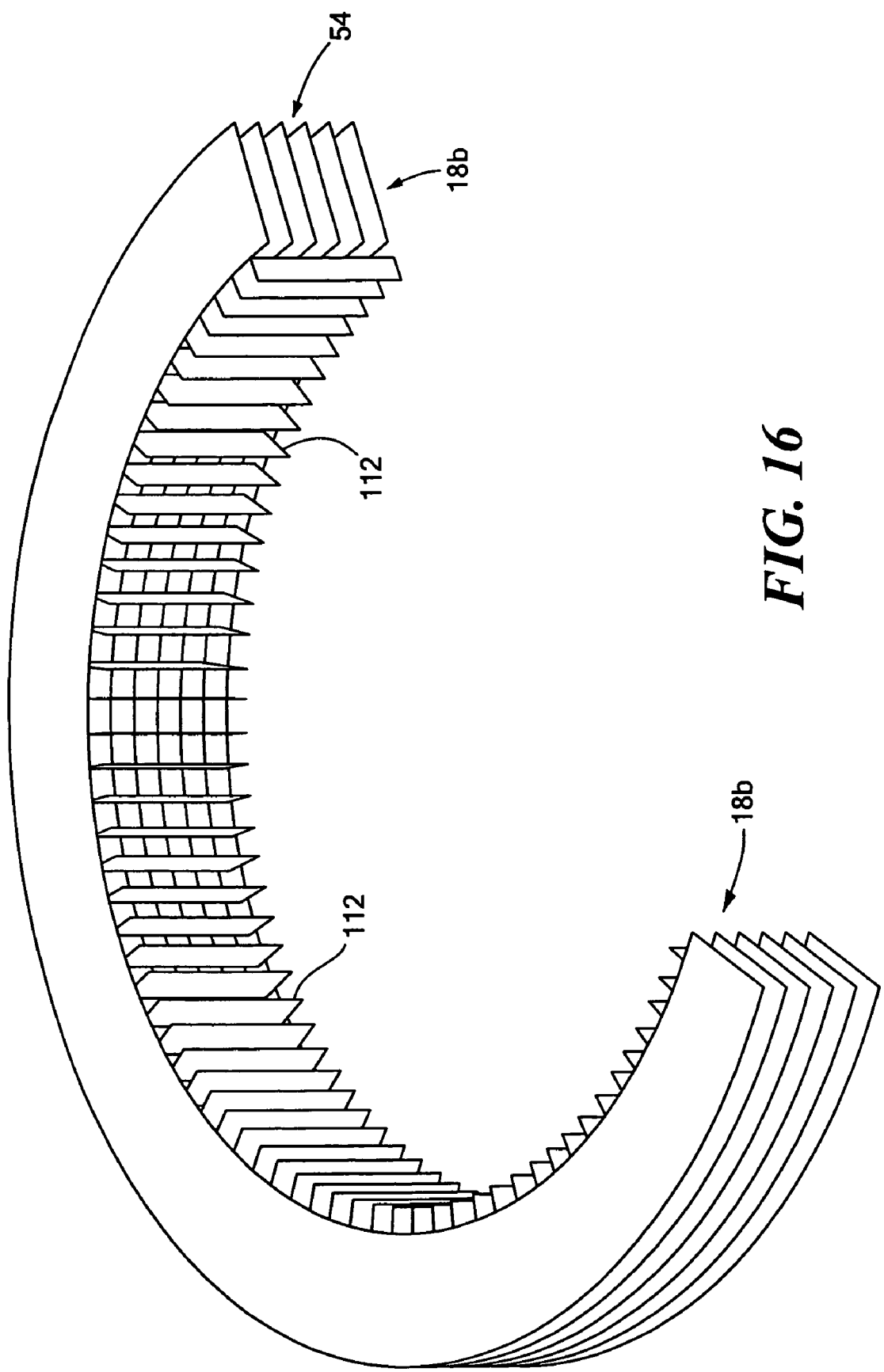
FIG. 16 is a three-dimensional side view showing in further detail one embodiment of the collimator subsystem shown in FIG. 15.

In this example, integrated SPECT/TCT system 10*a* includes source of radiation 90, typically enclosed in housing 91, FIG. 1 that emits fan-beam 102, FIG. 15, of radiation photons towards and encompassing large three-dimensional PIV 42*c* and the thorax of patient 26. PIV 42*c* is much larger than the imaging volume used in SPECT imaging, e.g., about 42 cm in diameter. Collimator subsystem 18*b*, having a plurality of vertical slats 112 that are spaced and angled to define the plurality of longitudinal slits 99 to define PIV 42*c* and for transversely collimating beam 102 of radiation photons. In one design, the longitudinal widths of slits 99 may have non-uniform widths for focusing on the source of radiation 90 to optimize collimation of beam 102 of radiation photons. FIG. 16 shows in further detail one embodiment of the structure of vertical slats 112 of collimator subsystem 18*b*. In one example, each vertical slat 112 is a thin piece of lead foil, e.g., about 0.2 mm in thickness, 15-20 mm in radial depth, 170 mm in vertical length, and separated from its adjacent vertical slats 112 by 3-4 mm thick Styrofoam plates for structural integrity.

Ideally, vertical slats 112, FIGS. 15 and 16 are configured to aim at source 90, FIG. 15, of radiation photons to improve transverse collimation of beam 102 of radiation photons. Vertical slats 112 also block scattered radiation photons from beam 102 from reaching detector subsystem 20 as well as any emissions photons from patient 26, e.g., from radiopharmaceutical used in SPECT imaging.

Patient positioning subsystem 12, FIG. 1 positions patient 26 to predetermined central axis 38, FIG. 15, of three-dimensional PIV 42*c* and intermittently and incrementally rotates patient 26 about axis 38 to generate a plurality of TCT projections, discussed in further detail below. Detector subsystem 20 detects the collimated radiation photons from collimator subsystem 18 and generates electrical signals that are processed by computer subsystem 25, FIG. 2 to obtain a plurality of TCT images.

Figure 17:
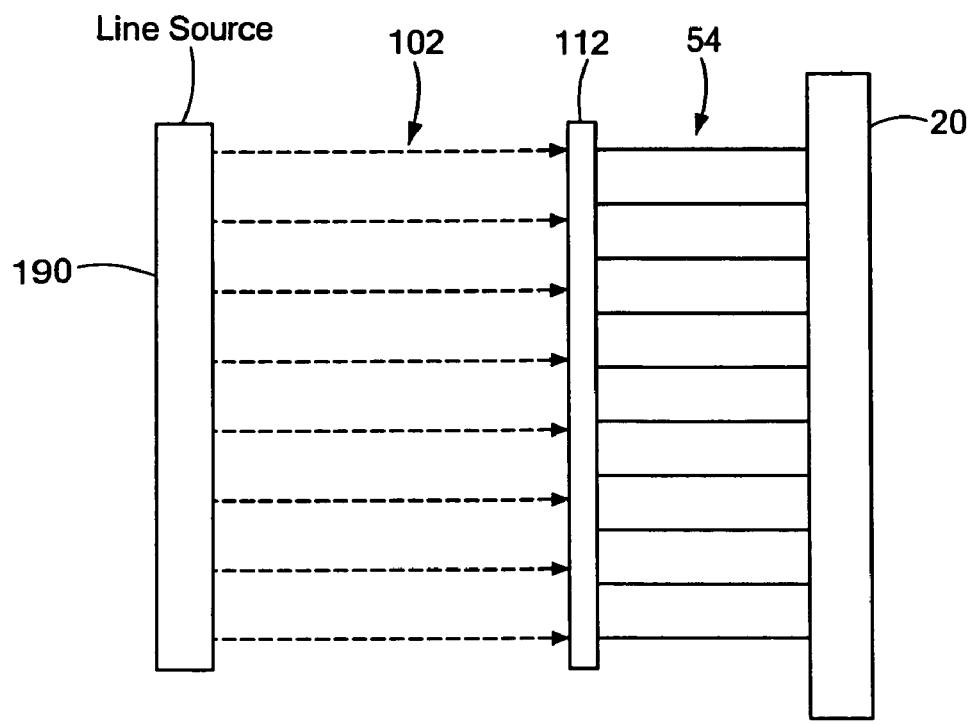
FIG. 17 is a schematic side view of one embodiment of the collimator subsystem shown in FIG. 15 and an example of a line source used for the source of radiation photons.

In one design, source of radiation 90, FIG. 15 may be line-source 190, FIG. 17, where like parts have been given like numbers. Line source 190, preferably includes a small longitudinal section of transversely parallel-slats (not shown) that function as its collimator (of similar design to the slats 54, FIGS. 4, 5, and 16). Line source 190 emits three-dimensional fan-beam 102 of radiation photon, as better shown in FIG. 15, which encompasses three-dimensional PIV 42*c*, and the thorax of patient 26. In one example, line source 190 is a commercially available Gd-153 source (e.g., about 100 keV photons), which can have a total activity up to 0.8 Ci or more.

Figure 18:
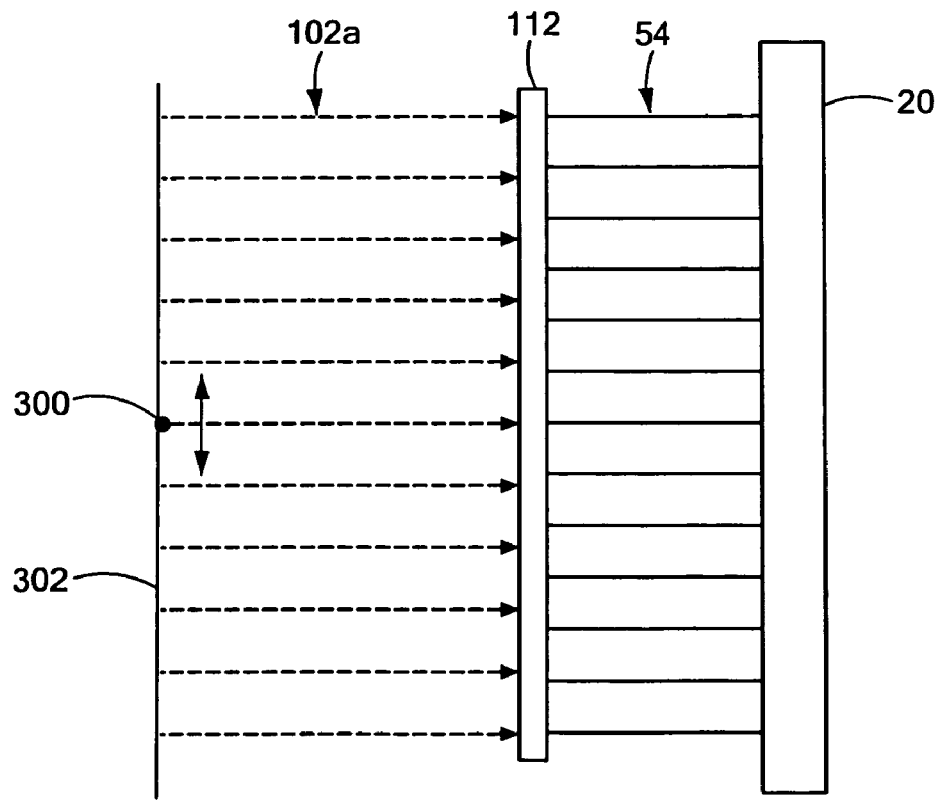
FIG. 18 is a schematic side view of the one embodiment of the collimator subsystem shown in FIG. 15 and an example of a longitudinal scanning point source used for the source of radiation photons.

Source of radiation 90, FIG. 15 may be a longitudinal scanning point source 300, FIG. 18, where like parts have been given like numbers. Longitudinal scanning point source 300 moves up and down on longitudinal axis 302, to generate three-dimensional fan-beam 102*a* (similar to fan beam 102, FIG. 17) of radiation photons, as better shown in FIG. 15, which encompasses three-dimensional PIV 42*c* and the thorax of patient 26. In this example, longitudinal scanning point source 300, FIG. 18, is preferably a source of radiation with high concentration and radiation flux, e.g., commercially available Gd-153 source (e.g., about 100 keV photons) or other more commonly available radionuclides, such as Tc-99m, which can have a total activity up to 50 mCi or more. The short-lived source like Tc-99m has the advantage of easy availability in many imaging labs, but it lasts only for a few hours. Another option for the transmission point source 300 is to use medium energy radionuclides, such as Ba-133 (356 keV), I-131 (364 keV), or In-111 (247 and 172 keV), as long as they can be packed in a small volume, such as in 3×3×3 mm$^3$ or less. These medium energy photons can penetrate both vertical and transverse slats of the collimator system and provide cone-beam sampling of the PIV 42*c*. When the point source is moving to several different longitudinal positions on its axis 302, the additional cone-beam sampling could be used to reduce artifacts in TCT's image reconstruction. The activity and concentration level of these medium energy sources can be reduced to 3-20 mCi range because they operate as if no collimator is in place.

Figure 19:
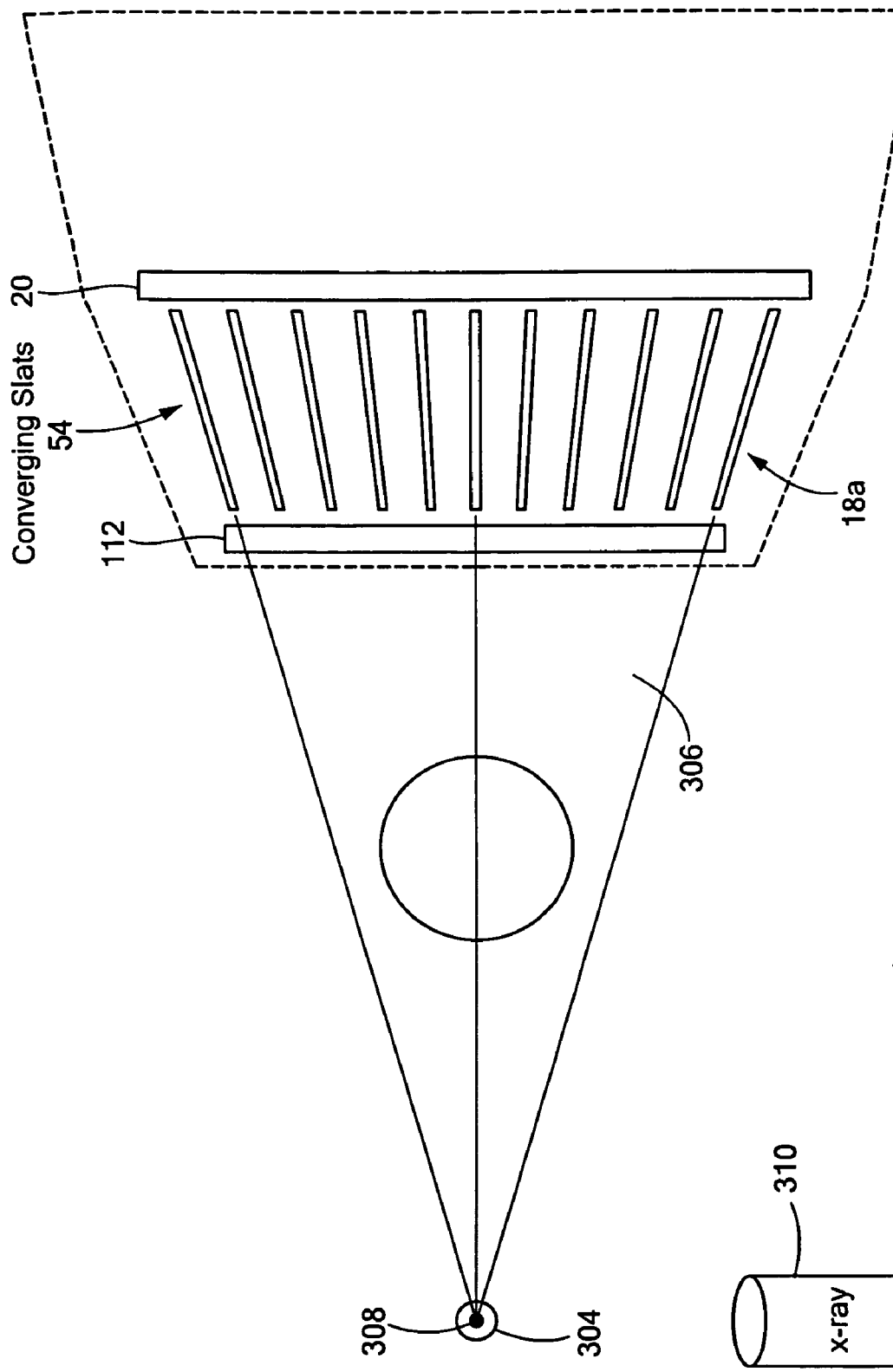
FIG. 19 is a schematic side view of another embodiment of the collimator subsystem shown in FIG. 15 incorporating converging slates and an example of a point used for the source of radiation photons.

In one preferred design, source of radiation 90, FIG. 15 may include point source 304, FIG. 19, where like parts have been given like numbers. Point source 304 generates three-dimensional cone-beam 306 of radiation photons that encompasses three-dimensional PIV 42*c*, FIG. 15 and the thorax of patient 26. In this example, point source 304, FIG. 19, is very small in size, e.g., 3×3×3 mm$^3$ or less. Therefore, point source 304 needs to be a strong source of radiation, e.g., commercially available Gd-153 source (e.g., about 100 keV photons), which can have a total activity up to 10 mCi or more. Other similar low energy radionuclides of comparable energy could also serve as transmission sources, although each comes with its own advantages and limitations, as described previously.

In order to effectively collimate cone-beam 306, FIG. 19, of radiation photons emitted from point source 304 and increase the amount of radiation photons detected by the detector subsystem 20, collimator subsystem 18*a*, similarly as discussed above with reference to FIG. 10, includes transversely spaced slats 54, FIG. 19, which converge on a predetermined focal points, shown in two dimensions as point 308, where point source 304 is located. Using converging slats 54 increases the solid angle of radiation photons received by detector subsystem 20 from small point source 304, when compared to parallel slats design of collimator subsystem 18b, FIGS. 15 and 16. The result is improved geometric sensitivity and improved TCT images. Moreover, because point source 304 (and longitudinal scanning point source 300, FIG. 18) is very small, it is less expensive, easier to handle, easier to replace, safer, reduces environmental hazards and has less strict protocols and radiation safety regulations.

Point source 304, FIG. 19, may include x-ray tube 310, e.g., a commercially available mini-X-ray tube, such as a Series 7000 by Oxford Instruments Inc, Scotts Valley, Calif. In this example, x-ray tube generates cone beam 306 of radiation photons that encompasses three-dimensional imaging volume 42c, FIG. 15 and patient 26. Because x-ray tube 310 can be turned off and on, the problems associated with line source 190, longitudinal scanning point source 300, or point source 304, discussed above, which continuously emits radiation photons, reduces its radiation flux with time, and requires regular replenishment, are eliminated. X-ray tube 310 is also less expensive, less complex, safer, and easier to replace than radionuclide transmission line source 190, FIG. 17, longitudinal scanning point source 300, FIG. 18, and point source 304, FIG. 19.

In one exemplary operation of integrated SPECT/TCT system 10a, FIG. 15, for TCT imaging, source of radiation 90 emits three-dimensional fan beam 102 of radiation photons (using line source 190 or longitudinal scanning point source 300 and collimator subsystem 18b as shown in FIGS. 17 and 18) or three-dimensional cone beam 306 (with point source 304 and collimator subsystem 18a as shown in FIG. 19) which encompasses three-dimensional PIV 42c, FIG. 15, and the thorax of patient 26 (shown in this example). Patient positing subsystem 12, FIG. 1 rotates patient 26, FIG. 15, approximately 120° about the central longitudinal axis 38, as shown by θ-320, in the direction indicated by arrow 322 and approximately 120°, indicated by θ-324, in the opposite direction indicated by arrow 326, e.g., for a total of about 240°. The ending positions of patient 26 after rotation of 120° in two directions is shown as phantom at 26a and 26b. The movement of patient 26 effectively allows fan-beam 102, or cone beam 306, FIG. 19 of radiation photons to sample PIV 42c, FIG. 15, over the major left side of the cross-section of patient 26, if not all of the thorax. The radiation photons are collimated by collimator subsystem 18a, 18b and cast a single TCT projection on detector system 20 at each incremental rotational step of the patient, as discussed above. Detector subsystem 20, FIG. 15, generates output electrical signals that are digitized and processed by a computer system 25, FIG. 1, to generate TCT images of patient 26, which are used to create attenuation maps for attenuation correction of SPECT images.

The high quality performance of integrated SPECT/TCT system 10a results, inter alia, from the high detected photon statistics, which is, in turn, the result of high radiation flux of the transmission source, and the high detection rate capability of the detector system 20. The latter is attributable to the detector system's modular design that allows parallel detection and processing.

Figure 20:
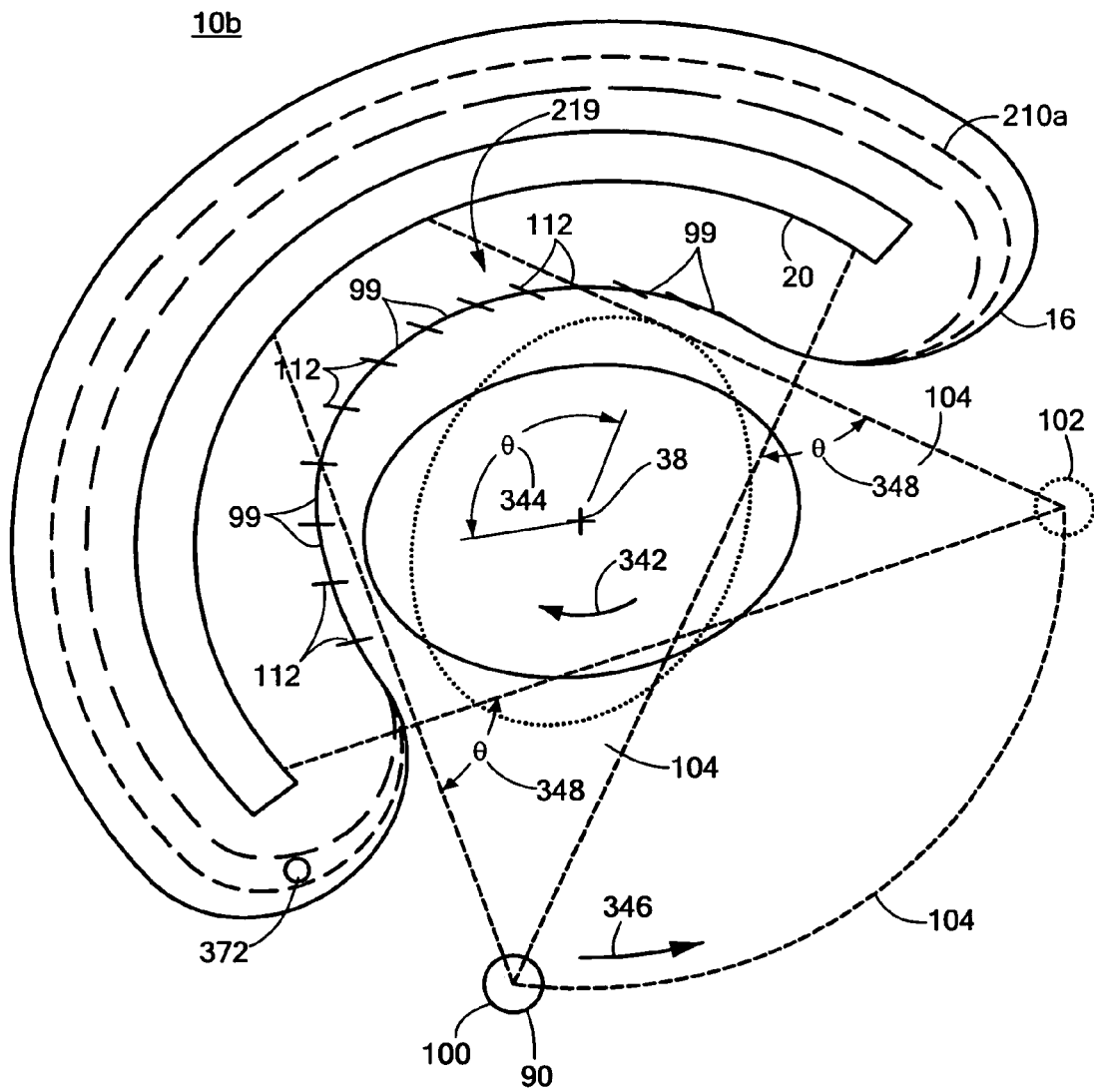
FIG. 20 is a schematic top view of another embodiment of this invention used for TCT imaging of very large patient incorporating a movable source of radiation photons.

In another embodiment of this invention, TCT system 10b, FIG. 20, of this invention includes movable source of radiation 90 which emits beam 104 of radiation photons. Source of radiation 90 may be line source 190, FIG. 17, longitudinal scanning point source 300, FIG. 18 or point source 304, FIG. 19. In this example, movable source of radiation 90, FIG. 20, is a line source, similar as shown in FIG. 17. Source of radiation 90, FIG. 20, is rotated in one direction about central longitudinal axis 38, e.g., in the direction indicated by arrow 346 on path 104 for about 120°, indicated by θ-348. Patient position subsystem 12, FIG. 1, rotates patient 26, FIG. 20, in the opposite direction of source of radiation 90 about the central longitudinal axis 38, e.g., in the direction indicated by arrow 342 for about 120°, as indicated by θ-344. Source of radiation 90 is shown at its start position at 100 and at its end position at 102. Patient 26 is shown at its start position by solid lines and at its end position in dashed lines.

The simultaneous and opposite movement of source of radiation 90 and patient 26 generates a plurality of TCT projections on detector subsystem 20. Detector subsystem 20 generates output electrical signals which are digitized and processed by a computer system to generate high quality TCT images of patient 26, which are used to reconstruct attenuation maps for attenuation correction of SPECT images, as discussed above with reference to FIGS. 1-13. The simultaneous and opposite movement of source of radiation 90 and patient 26 effectively allows fan-beam 102 of radiation photons to sample the cross-section of very large patients, e.g., when patient 26 is larger than fan beam 104. This is because for very large patient 26, the opening of frame 12 may not be large enough for very large patient 26 to 240° as described previously. By limiting the patient rotation to 120° and having the transmission source 90 share the remaining of 120°, the same 240° rotation is effectively achieved In one design, vertical slats 112, FIG. 20, which define the plurality of longitudinal slits 99, as discussed above with reference to FIGS. 15 and 16, are configured as section 219 on movable loop 210a, FIGS. 15 and 20, similar as discussed above with reference to FIG. 11. Section 219 is slideably coupled to frame 16. In this example, movable loop 210a, FIG. 20, is moved so that vertical slats 112 are continuously aimed at moving source of radiation 90 to improve transverse collimation of beam 102 of radiation photons: as source of radiation 90 moves in direction 346 along path 104, vertical slats 112 on movable loop 210 will move as a whole in synchrony with and in the same direction 346 as source of radiation 90 to maintain the individual aims of each slat 112 towards source of radiation 90.

Figure 21:
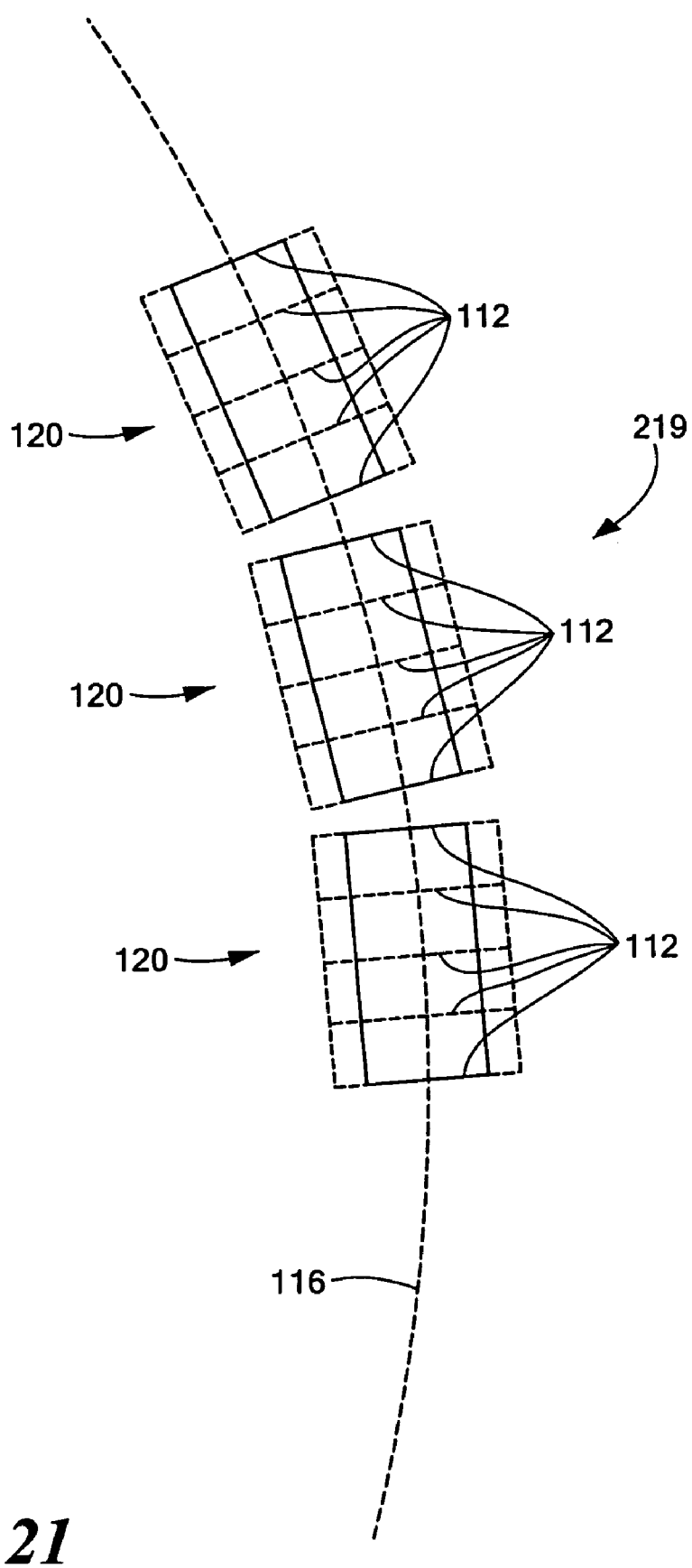
FIG. 21 is a schematic top view of one embodiment of movable sections used to drive the movable loop shown in FIG. 20 in order to aim the vertical slats of the collimator subsystem at the movable line source.
Figure 22:
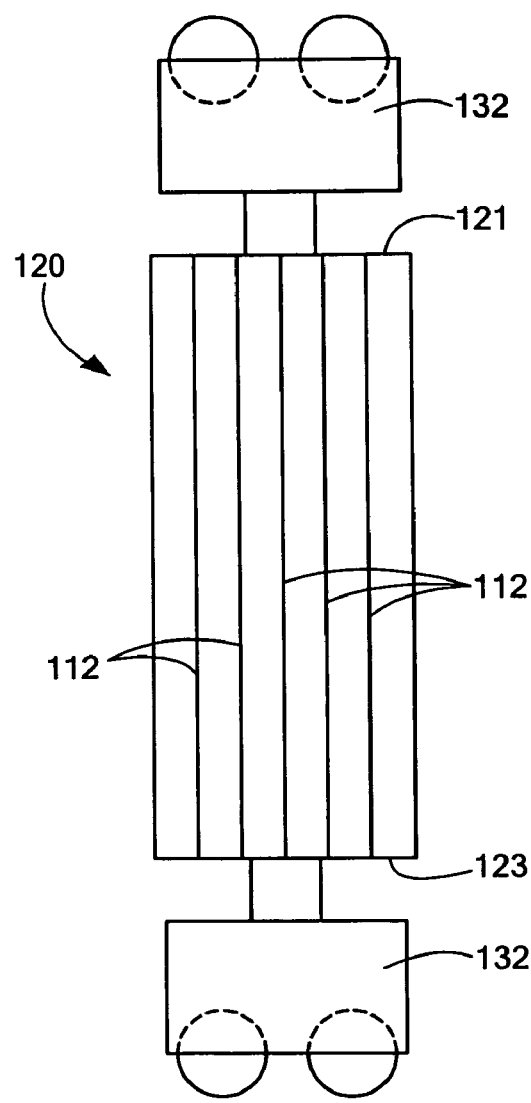
FIG. 22 is a schematic front view of one embodiment the movable sections shown in FIG. 21.
Figure 23:
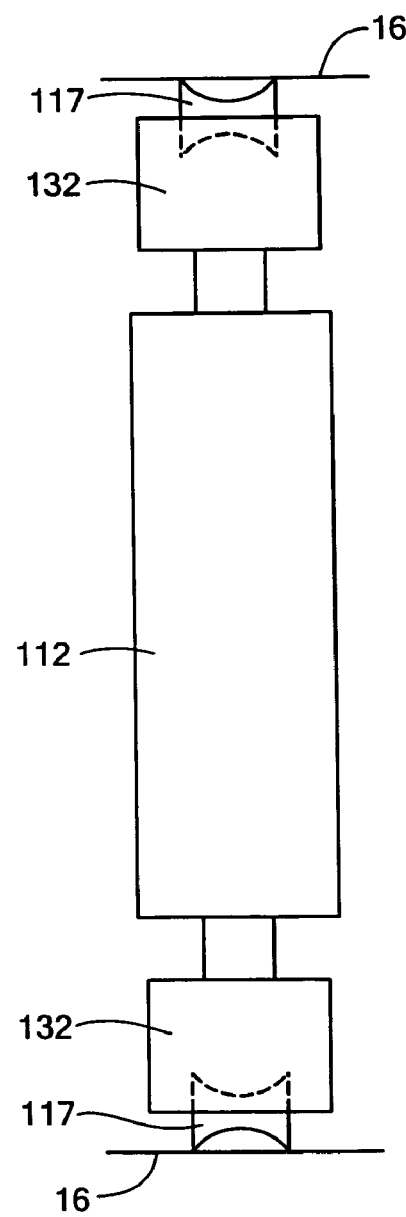
FIG. 23 is a schematic end view of one of the movable sections shown in FIG. 22.

To facilitate rotation of vertical slats 112 on loop 210, section 219 is broken up to small sections. In one example, section 219 is preferably comprised of a plurality of subsections 221, FIG. 21 that each includes a predetermined number of vertical slats 112, e.g., 5 as shown, although sections 120 may include any number of vertical slats 112 as needed for TCT imaging. Sections 120 with vertical slats 112 are preferably disposed on movable cars 132, FIG. 22 coupled to frame 16 on top surface 121 and bottom surface 123. FIG. 23 shows an end view of an exemplary section 120 with vertical slats 112 attached to cars 132 slideably attached frame 16 by wheels 117. In operation, cars 114 are driven such that vertical slats 112 are continuously aimed at the movable source 90 of radiation with motor 372, FIG. 20.

In one exemplary operation of integrated SPECT/TCT system 10, FIGS. 1-13 of this invention, patient set-up and imaging proceeds as follows. After patient 26, FIG. 1 is secured in chair 13 of patient position subsystem 12 with chest restraints, patient 26 and chair 13 are first moved to a default position for scout-imaging, e.g., PIV 42b, FIG. 8, in the frame 16. Electronic control of the system 10 is provided by computer system 25, FIG. 1, having a monitor (not shown) for data visualization, as is known to those skilled in the art. Section 216, FIG. 11, with wider slits 52a on loop 210, e.g., as shown in greater detail in FIG. 5, is already in the front of collimator subsystem 18. Scout SPECT imaging of a large PIV 42b, FIG. 8, covering the lower thorax is immediately performed with the collimator subsystem 18. In about 30 seconds, three low-resolution real-time reconstructed SPECT images show up on the monitor for the three standard orthogonal slices across the center of the heart. The location of the heart 40 gradually becomes clear on all three slices as a distinct blurry disk. The operator may then be prompted to verify the computer identified three-dimensional center of the heart 40, as well as the general size of the heart, as indicated on the monitor with a 10 cm and a 14 cm circles as best matched references, the outline of two three-dimensional spheres superimposed on each of the three slices.

Approximately 1-2 minutes into acquisition, as the displayed three-dimension scout-SPECT images gain more statistics to confirm the match, the operator clicks a software control button to approve the center location and select the better-matched size of the sphere, presumably three-dimensional center and size of the PIV to be used for acquiring the next core SPECT imaging.

Following the necessary translations, patient position subsystem 12, FIG. 1, moves patient 26 in three-dimensions to center the heart 40 at the center 32, FIG. 2 of PIV 42, or PIV 42a, FIG. 3 and locks in place. At the same time, section 212, FIG. 11, with PIV 42 on loop 210, or section 214 with PIV 42a on loop 210, for a larger patient 26, or for a larger heart, is moved to the front of collimator subsystem 18. As soon as the patient motion stops and the high resolution collimator subsystem 18, FIGS. 2 and 3, is properly configured, core SPECT imaging of heart 40 begins with a large number of projections acquired from multiple directions simultaneously for 0.5 to 2 minutes. In an alternative embodiment, scout imaging may be performed using acquired raw projections to determine the 3D center and the size of the heart without SPECT image reconstruction.

When acquiring high-resolution core SPECT images of heart 40, the required rotation of patient is a small angle rotation utilizing only several additional (2-5) steps. Patient positioning subsystem 25 rotates patient 26, for example, about 3° per step for a total of 15° in five additional steps. Thus, for a collimator system as shown in FIG. 24, a total of 72 to 78 projections may be acquired in 3 to 12 minutes.

Figure 14:
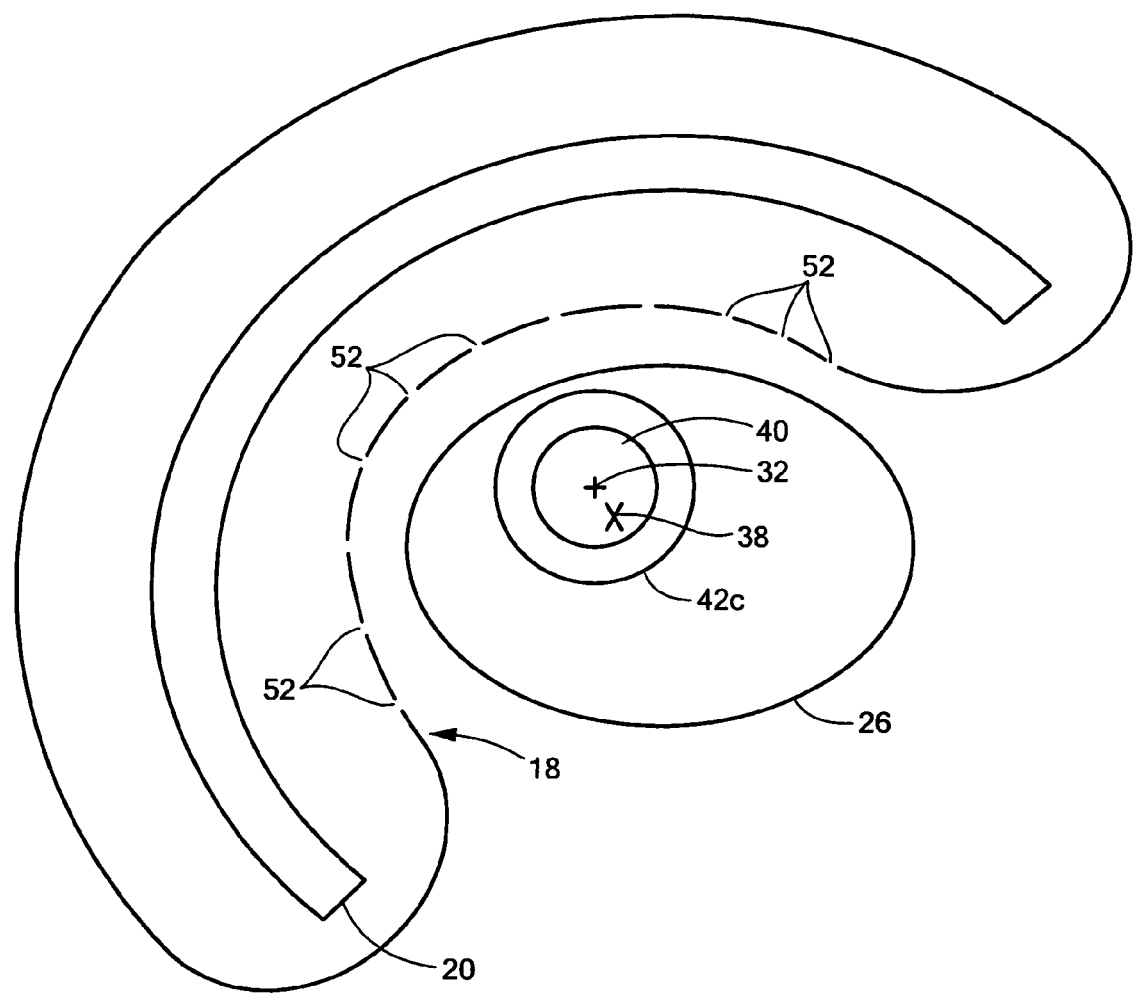
FIG. 14 is a schematic top diagram showing a center of a three-dimensional PIV used for SPECT imaging and another center of a three-dimensional PIV used for TCT imaging in accordance with this invention.

For the subsequent TCT operation, patient position subsystem 12 shifts patient laterally to bring the axis and center of anatomy of interest to the pre-defined TCT axis, e.g, central longitudinal axis that passes through center 38, FIG. 14, for acquisition of TCT images, using system 10a, 10b, FIGS. 15 and 20. The TCT images of the torso of patient 26 are used for attenuation correction of pre-corrected core SPECT images.

The result is system 10, FIGS. 1-14, is capable of achieving high performance and has significant advantages over the current state-of-the-art integrated SPECT/FCT systems. These advantages include, inter alia, high quality SPECT images of the heart, added scout imaging for a quick survey the location and size of the heart, increased overall detection efficiency, inherent detector stability, mechanical simplicity, the ability to define multiple PIVs to accommodate both typical and larger patients which accommodates the majority of patients of a patient population, compact physical size, predictable and reproducible performance, simple, practical, standardized and automated clinical operations, high count-rate performance, and integrated TCT for deriving high quality attenuation maps, and thus high quality attenuation-correction on SPECT images. Further, the small footprint of the system meets the need of hospitals and physician offices to reach a large patient population.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An integrated single photon emission computed tomography (SPECT)/transmission computed tomography (TCT) system for cardiac imaging comprising:
    a stationary open arc-shaped frame;
    a stationary open arc-shaped collimator subsystem for optimizing collimation of radiation photons emitted from the heart, the collimator subsystem configured to: approximately match the shape of the thoracic contour of patients having different sizes and weights, position the collimator subsystem closely proximate the heart of a patient, and define a plurality of predetermined imaging volumes each having a central longitudinal axis, each of the plurality of predetermined imaging volumes configured to encompass the heart of patients of different sizes and weights;
    a stationary arc-shaped detector subsystem proximate to the collimator subsystem and having a shape generally matching the shape of the collimator subsystem and configured to detect collimated radiation photons from the collimator subsystem and generate output electrical signals;
    a patient positioning subsystem configured to position the patient about and/or up and down the central longitudinal axis of a selected imaging volume of the plurality of predetermined imaging volumes and configured to intermittently and incrementally rotate the patient about a selected central longitudinal axis; and
    a computer subsystem configured to receive digitized output electrical signals from the detector subsystem and generate a plurality of SPECT or TCT images of the heart.

2. The system of claim 1 in which the shape of the collimator subsystem and the detector subsystems optimize collimation and detection of the radiation photons for a majority of the patients of a patient population.

3. The system of claim 1 in which each of the plurality of predetermined imaging volumes include a three-dimensional cylindrical imaging volume.

4. The system of claim 1 in which the arc-shaped frame, the collimator system, and the detector subsystem are subtended at an angle in the range of about 180° to 220° with respect to the center of each of the plurality of predetermined imaging volumes.

5. The system of claim 1 in which the collimator subsystem includes a slit-plate comprising a predetermined number of spaced longitudinal slits each having a predetermined width for transversely collimating the radiation photons.

6. The system of claim 5 in which the predetermined width of each of the plurality of spaced longitudinal slits is configured to adjust spatial resolution of transverse collimation.

7. The system of claim 6 further including a plurality of slit-guides attached proximate each side of each of the plurality of longitudinal slits.

8. The system of claim 7 in which the angle of the slit-guides and the location of the spaced longitudinal slits are configured to provide a plurality of non-overlapping projections which define the size and location of the plurality of predetermined imaging volumes.

9. The system of claim 8 in which the size and location of each of the plurality of predetermined imaging volumes and the plurality of non-overlapping projections provides high geometric efficiency in the detection of radiation photons emitted from the heart.

10. The system of claim 8 in which each of the plurality of predetermined imaging volumes are configured for patients having different thoracic contours and/or different sized hearts and/or different locations of the heart relative to a predefined central axis.

11. The system of claim 1 in which the plurality of predetermined imaging volumes includes a small three-dimensional imaging volume for generating SPECT images of the heart.

12. The system of claim 11 in which the combination of the location of spaced longitudinal slits, the angle of the slit-guides, and the distance between the slit-plate and the detector subsystem are adjusted for minification of a plurality of simultaneous non-overlapping projections cast on the detection system to provide high geometric efficiency for generating one or more SPECT images.

13. The system of claim 12 in which the one or more SPECT images are obtained by using image reconstruction of the plurality of simultaneous non-overlapping projections.

14. The system of claim 8 in which the collimator subsystem includes a plurality of transversely spaced slats disposed behind the slit-plate for longitudinally collimating the radiation photons.

15. The system of claim 14 in which the location of each of the plurality of transversely spaced slats is configured to adjust spatial resolution of longitudinal collimation.

16. The system of claim 15 in which the transversely spaced slats are configured to converge on predetermined focal points of a cone-beam of radiation photons emitted from the heart for increasing the number of radiation photons detected by the detector subsystem.

17. The system of claim 16 in which a patient positioning subsystem positions the patient up and/or down about the central longitudinal axis of one of the plurality of imaging volumes to acquire additional TCT imaging data in a longitudinal plane.

18. The system of claim 8 in which the slit-plate is configured as a flexible loop moveably coupled to the frame having a plurality of sections each configured to provide a unique predetermined imaging volume having a predetermined size and location, and a spatial resolution.

19. The system of claim 18 in which a desired section of the flexible loop is positioned proximate and surrounding the at least one predetermined imaging volume of the patient by driving the flexible loop to a predetermined location on the collimator subsystem.

20. The system of claim 19 further including a plurality of connected flexible loops moveably coupled to the frame, each loop including a plurality of sections configured to provide a unique predetermined imaging volume of a predetermined size, location, and spatial resolution.

21. The system of claim 1 in which the plurality of predetermined imaging volumes include a large three-dimensional imaging volume for generating a scout SPECT image which estimates a three-dimensional center of the heart and the general size of the heart.

22. The system of claim 1 in which the patient positioning subsystem positions the patient to the central longitudinal axis of a selected imaging volume of the plurality of imaging volumes based on previous scout SPECT images of the heart.

23. The system of claim 22 in which the patient positioning subsystem incrementally rotates the patient about the central longitudinal axis of one of the plurality of predetermined imaging volumes to obtain a plurality of projection images of the heart.

24. The system of claim 23 in which the patient positioning subsystem intermittently and incrementally rotates the patient about the central longitudinal axis of a small imaging volume of the plurality of predetermined imaging volumes to obtain a plurality of sequentially acquired sets of simultaneous projections and reconstructing a one or more SPECT images.

25. The system of claim 1 further including a source of radiation for emitting a beam of radiation photons towards and encompassing a large predetermined three-dimensional TCT imaging volume that encompasses the thorax of the patient.

26. The system of claim 25 in which the collimator system includes a plurality of vertical slats configured to define a plurality of longitudinal slits of a predetermined width for transversely collimating the beam of radiation photons.

27. The system of claim 26 in which the plurality of longitudinal slits have non-uniform widths for focusing on the source of radiation and optimizing collimation of the radiation photons emitted from the source of radiation.

28. The system of claim 27 in which the vertical slats are configured to aim at the source of radiation.

29. The system of claim 28 in which the collimator subsystem includes a plurality of transversely spaced parallel slats disposed behind the vertical slats for longitudinally collimating the beam of radiation photons.

30. The system of claim 29 in which the distance between each of the plurality of transversely spaced slats is configured to adjust spatial resolution of longitudinal collimation.

31. The system of claim 30 in which the source of radiation photons includes a longitudinal line source for emitting a three-dimensional fan beam of radiation photons which encompasses the three-dimensional TCT imaging volume.

32. The system of claim 29 in which the source of radiation includes a longitudinal scanning point source configured to emit a three-dimensional fan beam of radiation photons which encompasses the three-dimensional imaging volume.

33. The system of claim 25 in which the source of radiation photons includes a point source for emitting a three-dimensional cone beam of radiation photons which encompasses a three-dimensional TCT imaging volume.

34. The system of claim 33 in which the collimator subsystem includes a plurality of transversely spaced slats converging longitudinally to the point source for collimating the cone beam of radiation photons and for increasing the amount of radiation photons detected by the detector subsystem.

35. The system of claim 33 in which the distance between each of the plurality of spaced converging slats is configured to adjust the spatial resolution of longitudinal collimation.

36. The system of claim 33 in which the point source includes an x-ray tube.

37. An integrated single photon emission computed tomography (SPECT)/transmission computed tomography (TCT) system for cardiac imaging comprising:
- a stationary open arc-shaped frame;
- a stationary open arc-shaped collimator subsystem for optimizing collimation of radiation photons emitted from the heart, the collimator subsystem configured to: approximately match the shape of the thoracic contour of patients having different sizes and weights, position the collimator subsystem closely proximate the heart of a patient, and define a plurality of predetermined imaging volumes each having a central longitudinal axis, each of the plurality of predetermined imaging volumes configured to encompass the heart of patients of different sizes and weights;
- a stationary arc-shaped detector subsystem proximate to the collimator subsystem and having a shape generally matching the shape of the collimator subsystem and configured to detect collimated radiation photons from the collimator subsystem and generate output electrical signals;
- a patient positioning subsystem configured to position the patient about and/or up and down the central longitudinal axis of a selected imaging volume of the plurality of predetermined imaging volumes and configured to intermittently and incrementally rotate the patient about a selected central longitudinal axis; and
- a movable source of radiation for emitting a beam of radiation photons to and encompassing a selected imaging volume of the plurality of imaging volumes;
- a computer subsystem configured to receive digitized output electrical signals from the detector subsystem and generate a plurality of SPECT or TCT images of the heart.

38. The system of claim 37 wherein the movable point source is rotated in one direction about the central longitudinal axis and the patient is rotated in an opposite direction about the same central longitudinal axis for generating a plurality of TCT images.

39. An integrated single photon emission computed tomography (SPECT)/transmission computed tomography (TCT) system for cardiac imaging comprising:
- a stationary open arc-shaped frame;
- a stationary open arc-shaped collimator subsystem for optimizing collimation of radiation photons emitted from the heart, the collimator subsystem configured to: approximately match the shape of the thoracic contour of patients having different sizes and weights, position the collimator subsystem closely proximate the heart of said patients, and define a plurality of predetermined imaging volumes each having a central longitudinal axis, each of the plurality of predetermined imaging volumes configured to encompass the heart of patients of different sizes and weights; the collimator subsystem further including plurality of transversely spaced slats converging on a predetermined focal point of an x-ray source emitting a three-dimensional cone beam of radiation photons which encompasses a selected predetermined imaging volume of the plurality of predetermined imaging volumes;
- a stationary arc-shaped detector subsystem proximate to the collimator subsystem and having a shape generally matching the shape of the collimator subsystem and configured to detect collimated radiation photons from the collimator subsystem and generate output electrical signals;
- a patient positioning subsystem configured to position a patient about and/or up and down the central longitudinal axis of the a selected imaging volume of the plurality of predetermined imaging volumes and configured to intermittently and incrementally rotate the patient about a selected central longitudinal axis; and
- a computer subsystem configured to receive digitized output electrical signals from the detector subsystem and generate a plurality of SPECT or TCT images of the heart.

* * * * *